US012398179B2

(12) United States Patent
Pasquale

(10) Patent No.: US 12,398,179 B2
(45) Date of Patent: Aug. 26, 2025

(54) NANOMOLAR PEPTIDES AND DERIVATIVES TO DIFFERENTIALLY MODULATE EPHRIN RECEPTORS

(71) Applicant: Sanford Burnham Prebys Medical Discovery Institute, La Jolla, CA (US)

(72) Inventor: Elena B. Pasquale, San Diego, CA (US)

(73) Assignee: SANFORD BURNHAM PREBYS MEDICAL DISCOVERY INSTITUTE, La Jolla, CA (US)

(*) Notice: Subject to any disclaimer, the term of this patent is extended or adjusted under 35 U.S.C. 154(b) by 82 days.

(21) Appl. No.: 17/438,824

(22) PCT Filed: Mar. 13, 2020

(86) PCT No.: PCT/US2020/022765
§ 371 (c)(1),
(2) Date: Sep. 13, 2021

(87) PCT Pub. No.: WO2020/186218
PCT Pub. Date: Sep. 17, 2020

(65) Prior Publication Data
US 2022/0144893 A1 May 12, 2022

Related U.S. Application Data

(60) Provisional application No. 62/818,647, filed on Mar. 14, 2019.

(51) Int. Cl.
| | |
|---|---|
| *A61K 38/08* | (2019.01) |
| *A61K 38/00* | (2006.01) |
| *A61K 38/10* | (2006.01) |
| *A61K 47/56* | (2017.01) |
| *C07K 7/06* | (2006.01) |
| *C07K 7/08* | (2006.01) |

(52) U.S. Cl.
CPC ................ *C07K 7/08* (2013.01); *A61K 38/00* (2013.01)

(58) Field of Classification Search
CPC ........ A61K 38/00; A61K 38/08; A61K 38/10; A61K 47/56; C07K 7/06; C07K 7/08; C07K 14/715
See application file for complete search history.

(56) References Cited

U.S. PATENT DOCUMENTS

| | | | | |
|---|---|---|---|---|
| 8,361,510 B2 * | 1/2013 | Lyon | A61K 31/70 424/490 |
| 2004/0180823 A1 | 9/2004 | Pasquale et al. | |

FOREIGN PATENT DOCUMENTS

| | | |
|---|---|---|
| WO | WO-2006072787 A1 | 7/2006 |
| WO | WO-2013106824 A1 | 7/2013 |
| WO | WO-2019237075 A1 | 12/2019 |
| WO | WO-2020186218 A2 | 9/2020 |
| WO | WO-2022056473 A1 | 3/2022 |

OTHER PUBLICATIONS

Duggineni et al. Design and Synthesis of Potent Bivalent Pep-tide Agonists Targeting the EphA2 Receptor. ACS Med Chem Letters 4(3):344-348 (2013).
Lamberto et al. Development and Structural Analysis of a Nanomolar Cyclic Peptide Antagonist for the EphA4 Receptor. ACS Chem Biol 9(12):2787-2795 (2014).
Mitra et al. Structure—Activity Relationship Analysis of Peptides Targeting the EphA2 Receptor. Biochemistry 49(31):6687-6695 (2010).
Duggineni et al., Design and synthesis of potent bivalent peptide agonists targeting the EphA2 receptor. ACS Med Chem Lett. 4(3):344-348 (2013).
PCT/US2021/050294 International Search Report and Written Opinion dated Jan. 13, 2022.
Salem et al., Therapeutic targeting of pancreatic cancer via EphA2 dimeric agonistic agents. Pharmaceuticals (Basel) 13(5):90 [1-13] (2020).
Adams et al. Phenix: a comprehensive Python-based system for macromolecular structure solution. Acta Crystallogr D Biol Crystallogr 66:213-221 (2010).
Barquilla et al. Eph receptors and ephrins: therapeutic opportunities. Annu Rev Pharmacol Toxicol 55:465-87 (2015).
Boyd et al. Therapeutic targeting of EPH receptors and their ligands. Nat Rev Drug Discov. 13(1):39-62 (2014).
Chen et al. MolProbity: all-atom structure validation for macromolecular crystallography. Acta Crystallogr D Biol Crystallogr. 66(Pt 1):12-21 (2010).
Emsley et al. Features and development of Coot. Acta Crystallogr D Biol Crystallogr 66(Pt 4):486-501 (2010).
Gambini et al. Structure-Based Design of Novel EphA2 Agonistic Agents with Nanomolar Affinity in Vitro and in Cell. ACS Chem Biol. 13(9):2633-2644 (2018).
Gomez-Soler et al., Engineering nanomolar peptide ligands that differentially modulate EphA2 receptor signaling. Journal of Biological Chemistry 294(22):8791-8805 (2019).
Himanen et al. Ligand recognition by A-class Eph receptors: crystal structures of the EphA2 ligand-binding domain and the EphA2/ephrin-A1 complex EMBO Rep. 10(7):722-8 (2009).
Hughes et al., A highly specific monoclonal antibody against monkeypox virus detects the heparin binding domain of A27. Virology 464-465:264-273 (2014).

Laskowski et al. LigPlot+: multiple ligand-protein interaction diagrams for drug discovery. J Chem Inf Model. 51(10):2778-86 (2011).

(Continued)

*Primary Examiner* — Julie Ha
(74) *Attorney, Agent, or Firm* — WILSON SONSINI GOODRICH & ROSATI

(57) ABSTRACT

Disclosed herein are methods and compositions engineered to modulate EphA2, including novel peptides with unexpectedly high specificity and binding affinity. The compositions described herein can be attenuated to treat subjects suffering from diseases and/or conditions.

5 Claims, 14 Drawing Sheets

Specification includes a Sequence Listing.

(56) References Cited

OTHER PUBLICATIONS

Liebschner et al. Polder maps: improving OMIT maps by excluding bulk solvent. Acta Crystallogr D Struct Biol. 73(Pt 2):148-157 (2017).
Miao et al. Eph/ephrin signaling in epithelial development and homeostasis. Int J Biochem Cell Biol 41(4):762-70 (2009).
Murshudov et al. REFMAC5 for the refinement of macromolecular crystal structures. Acta Crystallogr D. Biol Crystallog. 67(Pt 4):355-367 (2011).
Noberini et al. Targeting Eph receptors with peptides and small molecules: progress and challenges. Semin Cell Dev Biol. 23(1):51-7 (2012).
Olson et al. Modifications of a Nanomolar Cyclic Peptide Antagonist for the EphA4 Receptor to Achieve High Plasma Stability. ACS Med Chem Lett 7(9):841-846 (2016).
Pasquale. Eph receptors and ephrins in cancer: bidirectional signalling and beyond. Nat Rev Cancer. 10(3):165-80 (2010).
Patil et al., Targeted delivery of YSA-functionalized and non-functionalized polymeric nanoparticles to injured pulmonary vasculature. Artificial Cells, Nanomedicine, and Biotechnology 46(sup3):S1059-S1066 (2018).
PCT/US2020/022765 International Invitation to Pay Additional Fees dated Jul. 20, 2020.
PCT/US2020/022765 International Search Report and Written Opinion dated Sep. 29, 2020.
Riedl et al. Targeting the Eph System with Peptides and Peptide Conjugates. Curr Drug Targets. 16(10):1031-47 (2015).
Singh et al., The EphA2 receptor is activated through induction of distinct, ligand-dependent oligomeric structures. Communications Biology 1:15 [1-12]; doi: 10.1038/s42003-018-0017-7 (2018).
Swierczewska et al., What is the future of PEGylated therapies? Expert Opinion on Emerging Drugs 20(4):531-536 (2015).
Wang et al., A novel targeted system to deliver chemotherapeutic drugs to EphA2-expressing cancer cells. Journal of Medicinal Chemistry 55(5):2427-2436 (2012).
Wu et al. Receptor-mediated in vitro gene transformation by a soluble DNA carrier system. J Biol Chem 262(10):4429-4432 (1987).

\* cited by examiner

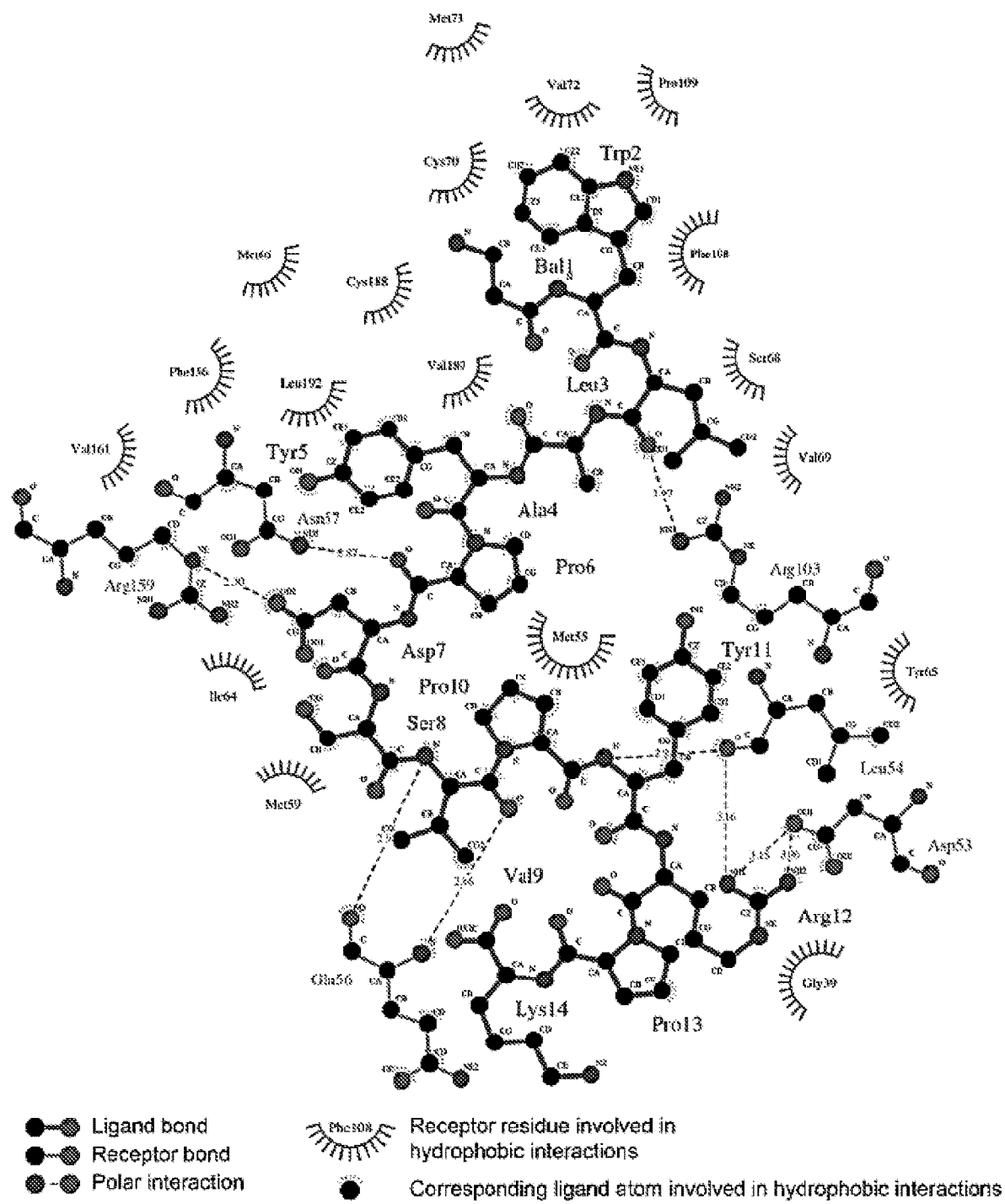

A  βA-WLA-YRPK-bio (mol D)
   βA-WLA-YRPK-bio (mol C)

B  βA-WLA-YRPK-bio
   YSA-GSGSK-bio

C  βA-WLA-YRPK-bio
   βA-WLA-Yam

D  βA-WLA-YRPK-bio
   βA-WLA-YSK-bio

E  βA-WLA-YRPK-bio
   135E2

F  βA-WLA-YRPK-bio C-ter
   135E2 C-ter

SEQUENCE LISTING

```
<160> NUMBER OF SEQ ID NOS: 38

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(2)
<223> OTHER INFORMATION: This region may encompass "Y-S" or "W-L"
<220> FEATURE:
<221> NAME/KEY: MISC_FEATURE
<222> LOCATION: (10)..(14)
<223> OTHER INFORMATION: This region may encompass "M-M-S" or "Mam" or
      "Yam" or "Y-K" or "Y-S-K" or "Y-G-S-K" or "Y-G-S-G-K" or "Y-R"
      or "Y-S"
<220> FEATURE:
<223> OTHER INFORMATION: See specification as filed for detailed
      description of substitutions and preferred embodiments

<400> SEQUENCE: 1

Xaa Xaa Ala Tyr Pro Asp Ser Val Pro Xaa Xaa Xaa Xaa Xaa
1               5                   10

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Tyr Gly Ser Lys
1

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Gly Ser Gly Lys
1               5

<210> SEQ ID NO 4
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 4

Gly Ser Gly Ser Lys
1               5

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Ser Ala Tyr Pro Asp Ser Val Pro Met
1               5                   10

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Ser Ala Tyr
1

<210> SEQ ID NO 7
<211> LENGTH: 4
<212> TYPE: PRT
<213> ORGANISM: Unknown
<220> FEATURE:
<223> OTHER INFORMATION: Description of Unknown:
      Ephrin-A1 sequence

<400> SEQUENCE: 7

Phe Thr Pro Phe
1

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Ala Tyr Pro Asp Ser Val Pro Phe Arg Pro
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala His His His His His His
1               5
```

-continued

```
<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Met Ala Ser Gln Gly Pro Gly
1               5

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Tyr Ser Ala Tyr Pro Asp Ser Val Pro Met Met Ser
1               5                   10

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Tyr Ser Ala Tyr Pro Asp Ser Val Pro Met Met Ser Gly Ser Gly Ser
1               5                   10                  15

Lys

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Tyr Ser Ala Tyr Pro Asp Ser Val Pro Met Met Ser Gly Ser Gly Ser
1               5                   10                  15

Lys

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Tyr Ser Ala Tyr Pro Asp Ser Val Pro Met Met Ser Lys
1               5                   10

<210> SEQ ID NO 15
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 15

Tyr Ser Ala Tyr Pro Asp Ser Val Pro Met
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Trp Leu Ala Tyr Pro Gly Ala Val Ser Tyr Arg
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Trp Leu Ala Tyr Pro Asp Ser Val Pro Met
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala

<400> SEQUENCE: 18

Ala Trp Leu Ala Tyr Pro Asp Ser Val Pro Met
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala

<400> SEQUENCE: 19

Ala Trp Leu Ala Tyr Pro Asp Ser Val Pro Tyr
1               5                   10

<210> SEQ ID NO 20
<211> LENGTH: 12
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala

<400> SEQUENCE: 20

Ala Trp Leu Ala Tyr Pro Asp Ser Val Pro Tyr Lys
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala

<400> SEQUENCE: 21

Ala Trp Leu Ala Tyr Pro Asp Ser Val Pro Tyr Ser Lys
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala

<400> SEQUENCE: 22

Ala Trp Leu Ala Tyr Pro Asp Ser Val Pro Tyr Ser Lys
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala

<400> SEQUENCE: 23

Ala Trp Leu Ala Tyr Pro Asp Ser Val Pro Tyr Gly Ser Lys
1               5                   10

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala
```

```
<400> SEQUENCE: 24

Ala Trp Leu Ala Tyr Pro Asp Ser Val Pro Tyr Gly Ser Gly Lys
1               5                   10                  15

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala

<400> SEQUENCE: 25

Ala Trp Leu Ala Tyr Pro Asp Ser Val Pro Tyr Arg
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala

<400> SEQUENCE: 26

Ala Trp Leu Ala Tyr Pro Asp Ser Val Pro Tyr Arg Pro Lys
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala

<400> SEQUENCE: 27

Ala Trp Leu Ala Tyr Pro Asp Ser Val Pro Tyr Arg Pro Lys
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala

<400> SEQUENCE: 28

Ala Trp Leu Ala Tyr Pro Asp Ser Val Pro Tyr Ser Pro Lys
1               5                   10

<210> SEQ ID NO 29
```

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala

<400> SEQUENCE: 29

Ala Trp Leu Ala Tyr Pro Asp Ser Val Pro Tyr Arg Pro Lys
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala

<400> SEQUENCE: 30

Ala Trp Leu Ala Tyr Pro Asp Ser Val Pro Tyr Arg Pro Lys
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala

<400> SEQUENCE: 31

Ala Trp Leu Ala Tyr Pro Asp Ser Val Pro Tyr Arg Pro Lys
1               5                   10

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Lys Ala Trp Leu Ala Tyr Pro Asp Ser Val Pro Tyr Arg Pro Lys
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Carbamidomethyl-cysteine
```

```
<400> SEQUENCE: 33

Cys Gly Ala Trp Leu Ala Tyr Pro Asp Ser Val Pro Tyr Arg Pro Lys
1               5                   10                  15

<210> SEQ ID NO 34
<211> LENGTH: 12
<212> TYPE: PRT
<213> ORGANISM: Unknown
<220> FEATURE:
<223> OTHER INFORMATION: Description of Unknown:
      Ephrin-A1 sequence

<400> SEQUENCE: 34

Phe Thr Pro Phe Thr Leu Gly Lys Glu Phe Lys Glu
1               5                   10

<210> SEQ ID NO 35
<211> LENGTH: 12
<212> TYPE: PRT
<213> ORGANISM: Unknown
<220> FEATURE:
<223> OTHER INFORMATION: Description of Unknown:
      Ephrin-A2 sequence

<400> SEQUENCE: 35

Phe Thr Pro Phe Ser Leu Gly Phe Glu Phe Arg Pro
1               5                   10

<210> SEQ ID NO 36
<211> LENGTH: 12
<212> TYPE: PRT
<213> ORGANISM: Unknown
<220> FEATURE:
<223> OTHER INFORMATION: Description of Unknown:
      Ephrin-A3 sequence

<400> SEQUENCE: 36

Tyr Ser Ala Phe Ser Leu Gly Tyr Glu Phe His Ala
1               5                   10

<210> SEQ ID NO 37
<211> LENGTH: 12
<212> TYPE: PRT
<213> ORGANISM: Unknown
<220> FEATURE:
<223> OTHER INFORMATION: Description of Unknown:
      Ephrin-A4 sequence

<400> SEQUENCE: 37

Phe Thr Pro Phe Ser Leu Gly Phe Glu Phe Leu Pro
1               5                   10

<210> SEQ ID NO 38
<211> LENGTH: 12
<212> TYPE: PRT
<213> ORGANISM: Unknown
<220> FEATURE:
<223> OTHER INFORMATION: Description of Unknown:
      Ephrin-A5 sequence

<400> SEQUENCE: 38

Phe Thr Pro Phe Ser Leu Gly Phe Glu Phe Arg Pro
1               5                   10
```

NANOMOLAR PEPTIDES AND DERIVATIVES TO DIFFERENTIALLY MODULATE EPHRIN RECEPTORS

CROSS-REFERENCE TO RELATED APPLICATIONS

This application is the U.S. National Stage application of International Application No. PCT/US2020/022765, filed on Mar. 13, 2020, and claims the benefit of U.S. Provisional Application No. 62/818,647, filed on Mar. 14, 2019, all of which are incorporated herein by reference in their entirety.

STATEMENT AS TO FEDERALLY SPONSORED RESEARCH

This invention was made with government support under R01 NS087070, P30 CA030199, and R01 GM131374 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on May 30, 2024, is named 42256-745_831_SL.txt and is 10,940 bytes in size.

BACKGROUND

EphA2 has been implicated in many disease processes. It is overexpressed in many cancer types where ligand-induced EphA2 kinase-dependent signaling is low (Barquilla and Pasquale, 2015; Miao and Wang, 2009; Pasquale, 2010). This apparent paradox can be explained by the fact that the receptor has pro-oncogenic activities in the absence of ligand. In contrast, EphA2 activation by ephrin-A ligands can inhibit oncogenic signaling networks (such as AKT-mTORC1 and RAS-ERK) and the pro-oncogenic EphA2 phosphorylation on S897 and induce EphA2 internalization and degradation. Thus, agents promoting EphA2 activation are useful to suppress cancer cell malignancy as well as to deliver drugs, toxins and imaging agents to tumor cells. Additionally, inhibiting EphA2 activation is useful against pathological forms of angiogenesis, inflammation and parasitic infections.

SUMMARY

Described herein are novel methods and compositions that are therapeutically effective in treating diseases, conditions, and/or subsets of diseases and conditions wherein the pathology of the disease, condition, or subset thereof involves the EphA2 receptor. EphA2 receptor activity contributes to many pathological conditions like cancer cell proliferation. Meanwhile, EphA2 receptor inhibition contributes to other pathological conditions like harmful inflammation and angiogenesis. The methods and compositions described herein provide novel techniques to modulate EphA2 activity to achieve a desired effect relative to the pathology experienced by the subject.

In some aspects of the peptides and methods described herein, disclosed is a method of treating a disease or condition in a subject comprising administering to the subject a therapeutically effective amount of a peptide comprising X1-A-Y-P-D-S-V-P-X2 (SEQ ID NO: 1) wherein X1 is Y-S or W-L; X2 is any one of M-M-S, Mam, Yam, Y-K, Y-S-K, Y-G-S-K (SEQ ID NO: 2), Y-G-S-G-K (SEQ ID NO: 3), Y-R, or Y-S; and a half-life extending molecule, the addition of which slows down excretion of the peptide from the subject. In some embodiments, the peptide further comprises a GSGSK linker (SEQ ID NO: 4) on a carboxyl terminus ("C-terminal"). In some embodiments, the peptide further comprises biotin on the C-terminal. In some embodiments, the peptide further comprises a β-A (Alanine) on an amino terminus ("N-terminal"). In some embodiments, the peptide further comprises P-K on a carboxyl terminus ("C-terminal"). In some embodiments, the C-terminal of the peptide is amidated. In some embodiments, the peptide further comprises acetylation of a Lys14 side chain. In some embodiments, the peptide further comprises a biotinylated alanine on an amino terminus ("N-terminal"). In some embodiments, the peptide comprises any combination of further components described herein.

In another aspect, the methods disclosed herein comprise a method of treating a subtype of a disease or condition in a subject comprising administering to the subject a therapeutically effective amount of a peptide comprising X1-A-Y-P-D-S-V-P-X2 (SEQ ID NO: 1), wherein X1 is Y-S or W-L; X2 is any one of M-M-S, Mam, Yam, Y-K, Y-S-K, Y-G-S-K (SEQ ID NO: 2), Y-G-S-G-K (SEQ ID NO: 3), Y-R, or Y-S; and a half-life extending molecule, the addition of which slows down excretion of the peptide from the subject. In some embodiments, the peptide further comprises a GSGSK linker (SEQ ID NO: 4) on a carboxyl terminus ("C-terminal"). In some embodiments, the peptide further comprises biotin on the C-terminal. In some embodiments, the peptide further comprises a B-A (Alanine) on an amino terminus ("N-terminal). In some embodiments, the peptide further comprises P-K on a carboxyl terminus ("C-terminal"). In some embodiments, the C-terminal of the peptide is amidated. In some embodiments, the peptide further comprises acetylation of a Lys14 side chain. In some embodiments, the peptide further comprises a biotinylated alanine on an amino terminus ("N-terminal"). In some embodiments, the peptide comprises any combination of further components described herein. In another aspect, the methods disclosed herein comprise a method of preventing or reversing the onset of a subset of a disease or condition in a subject suffering from a disease or condition comprising administering to the subject a therapeutically effective amount of a peptide comprising X1-A-Y-P-D-S-V-P-X2 (SEQ ID NO: 1), wherein X1 is Y-S or W-L; X2 is any one of M-M-S, Mam, Yam, Y-K, Y-S-K, Y-G-S-K (SEQ ID NO: 2), Y-G-S-G-K (SEQ ID NO: 3), Y-R, or Y-S; and a half-life extending molecule, the addition of which slows down excretion of the peptide from the subject. In some embodiments, the peptide further comprises a GSGSK linker (SEQ ID NO: 4) on a carboxyl terminus ("C-terminal). In some embodiments, the peptide further comprises biotin on the C-terminal. In some embodiments, the peptide further comprises a B-A (Alanine) on an amino terminus ("N-terminal"). In some embodiments, the peptide further comprises P-K on a carboxyl terminus ("C-terminal"). In some embodiments, the C-terminal of the peptide is amidated. In some embodiments, the peptide further comprises acetylation of a Lys14 side chain. In some embodiments, the peptide further comprises a biotinylated alanine on an amino terminus ("N-terminal"). In some embodiments, the peptide comprises any combination of further components described herein. In some embodiments, the disease or condition is a parasitic infection. In some embodiments, the disease or condition is pathological forms of angiogenesis. In some embodiments, the disease or condition comprises an inflammatory disease. In some embodiments, the inflammatory disease is atherosclerosis. In some embodiments, the disease or condition is cancer. In some embodiments, the cancer comprises prostate cancer, castration resistant prostate cancer, neuroendocrine prostate cancer, transitional cell (or urothelial) prostate cancer, squamous cell prostate cancer, small cell prostate cancer, or a combination thereof.

In another aspect, the compositions disclosed herein comprise a composition comprising a peptide comprising X1-A-Y-P-D-S-V-P-X2 (SEQ ID NO: 1), wherein X1 is Y-S or W-L; and X2 is any one of M-M-S, Mam, Yam, Y-K, Y-S-K, Y-G-S-K (SEQ ID NO: 2), Y-G-S-G-K (SEQ ID NO: 3), Y-R, or Y-S. In some embodiments, the peptide further comprises a GSGSK linker (SEQ ID NO: 4) on a carboxyl terminus ("C-terminal"). In some embodiments, the peptide further comprises biotin on the C-terminal. In some embodiments, the peptide further comprises a B-A (Alanine) on an amino terminus ("N-terminal"). In some embodiments, the peptide further comprises P-K on a carboxyl terminus ("C-terminal"). In some embodiments, the C-terminal of the peptide is amidated. In some embodiments, the peptide further comprises acetylation of a Lys14 side chain. In some embodiments, the peptide further comprises a biotinylated alanine on an amino terminus ("N-terminal"). In some embodiments, the peptide comprises any combination of further components described herein.

In another aspect, the compositions disclosed herein comprise a composition comprising a peptide comprising X1-A-Y-P-D-S-V-P-X2 (SEQ ID NO: 1), wherein X1 is Y-S or W-L; X2 is any one of M-M-S, Mam, Yam, Y-K, Y-S-K, Y-G-S-K (SEQ ID NO: 2), Y-G-S-G-K (SEQ ID NO: 3), Y-R, or Y-S; and a half-life extending molecule, the addition of which slows down excretion of the peptide from a subject to which the peptide is administered. In some embodiments, the peptide further comprises a GSGSK linker (SEQ ID NO: 4) on a carboxyl terminus ("C-terminal"). In some embodiments, the peptide further comprises biotin on the C-terminal. In some embodiments, the peptide further comprises a B-A (Alanine) on an amino terminus ("N-terminal"). In some embodiments, the peptide further comprises P-K on a carboxyl terminus ("C-terminal"). In some embodiments, the C-terminal of the peptide is amidated. In some embodiments, the peptide further comprises acetylation of a Lys14 side chain. In some embodiments, the peptide further comprises a biotinylated alanine on an amino terminus ("N-terminal"). In some embodiments, the peptide comprises any combination of further components described herein. In some embodiments, the composition further comprises a carrier, such as a pharmaceutically acceptable carrier.

In another aspect, the methods disclosed herein comprise a method of preventing oligomerization of an EphA2 receptor comprising contacting the EphA2 receptor with a composition comprising a peptide comprising X1-A-Y-P-D-S-V-P-X2 (SEQ ID NO: 1), wherein X1 is Y-S or W-L; and X2 is any one of M-M-S, Mam, Yam, Y-K, Y-S-K, Y-G-S-K (SEQ ID NO: 2), Y-G-S-G-K (SEQ ID NO: 3), Y-R, or Y-S. In some embodiments, the peptide further comprises a GSGSK linker (SEQ ID NO: 4) on a carboxyl terminus ("C-terminal"). In some embodiments, the peptide further comprises biotin on the C-terminal. In some embodiments, the peptide further comprises a B-A (Alanine) on an amino terminus ("N-terminal"). In some embodiments, the peptide further comprises biotin on a carboxyl terminus ("C-terminal"). In some embodiments, the peptide further comprises P-K on a carboxyl terminus ("C-terminal"). In some embodiments, the C-terminal of the peptide is amidated. In some embodiments, the peptide further comprises acetylation of a Lys14 side chain. In some embodiments, the peptide further comprises a biotinylated alanine on an amino terminus ("N-terminal"). In some embodiments, the peptide comprises any combination of further components described herein. In some embodiments, the composition further comprises a half-life extending molecule, the addition of which slows down excretion of the peptide from a subject to which the peptide is administered.

BRIEF DESCRIPTION OF THE DRAWINGS

The novel features of the methods and compositions described herein are set forth with particularity in the appended claims. A better understanding of the features and advantages of the present methods and compositions described herein will be obtained by reference to the following detailed description that sets forth illustrative embodiments, in which the principles of the methods and compositions described herein are utilized, and the accompanying drawings of which:

(FIG. 1A) YSA-GSGSK-bio peptide (SEQ ID NO: 12) in complex with the EphA2 LBD. The LBD is in grey and the portion of the peptide visible in the crystal structure (YSAYPDSVPM (SEQ ID NO: 5), corresponding to residues 1-10) and the biotin are in dark red. The DE, GH and JK loops of EphA2, which line the ephrin-binding pocket, are in dark grey. EphA2 is shown in ribbon representation and the peptide in stick representation (PDBID: 6NJZ). (FIG. 1B) Ephrin-A1 G-H loop in complex with the EphA2 LBD (PDBID: 3HEI). EphA2 is shown as in A and ephrin-Al is in pink. The GH loop of ephrin-A1, which binds to the ephrin-binding pocket, is indicated. (FIG. 1C) YSA peptide in complex with the EphA2 LBD as in panel A, but shown in surface representation and without the biotin. The peptide-EphA2 interface covers 777 Å2. (FIG. 1D) Ephrin-A1 G-H loop in complex with the EphA2 LBD as in panel B, but shown in surface representation. Only ephrin residues of the GH loop interacting with EphA2 (residues 111-119) are shown. Their buried interface covers 603 Å2. (FIG. 1E) YSA-GSGSK-bio (SEQ ID NO: 12) (the peptide backbone is shown as ribbon and side-chains as sticks) in complex with the EphA2 LBD (in surface representation). N-ter indicates the N-terminus of the peptide. (FIG. 1F) Overlay of the structure of the YSA-GSGSK-bio (SEQ ID NO: 12) and the ephrin-Al G-H loop in ribbon representation. The side chains of the YISAY4 sequence (SEQ ID NO: 6) of the peptide and the F111TPF114 sequence (SEQ ID NO: 7) of ephrin-Al are shown as sticks to highlight the extensive overlap of these regions. (FIG. 1G) Alignment of the YSA (SEQ ID NO: 11) and SWL peptides (SEQ ID NO: 16) with the G-H loop of ephrin-A ligands (SEQ ID NOS 34-38, respectively, in order of appearance). Asterisks mark the aromatic residues of the conserved WXXW motif. The peptide residues closely interacting with EphA2 in the crystal structure are colored in red. Ephrin-Al residues shown in panels D and F are colored in pink. (FIG. 1H) Detailed interactions of YSA (sticks) with EphA2 (cartoon and surface with interacting residues shown as grey sticks). Polar and hydrophobic interactions are indicated by green dashes. Key interacting residues are labeled.

(FIG. 2A) Representative ELISAs comparing the ability of the peptides to inhibit binding of ephrin-A5 fused to alkaline phosphatase (ephrin-A5 AP) to the immobilized EphA2 extracellular domain fused to the Fc portion of an antibody (EphA2 Fc). The graphs show averages±SE from triplicate measurements from a representative experiment. $IC_{50}$ values calculated from the fitted curves in each experiment are shown. Average $IC_{50}$ values from multiple experiments are shown in Table 1. All concentrations are nM and the 100 nM peptide concentration is outlined in red. (FIG. 2B) Ephrin-A5 AP binding to the indicated EphA receptors and ephrin-B2 AP binding to the indicated EphB receptors in the presence of the indicated peptide, normalized to ephrin binding without peptide. The bars show averages±SE from triplicate measurements. Figure discloses SEQ ID NOS 11-32, respectively, in order of appearance.

(FIG. 3A) Structure of the EphA2 LBD (grey surface with the DE, GH and JK loops that line the ephrin-binding pocket in dark gray) with the bA-WLA-Yam peptide (SEQ ID NO: 19) (peptide backbone shown as purple ribbon and side-chains as sticks). (FIG. 3B) Detailed interactions of bA-WLA-Yam peptide (SEQ ID NO: 19) (magenta sticks) with the EphA2 LBD (interacting residues shown as grey sticks). Polar and hydrophobic interactions are indicated by green dashes. Key interacting residues are labeled. (Figs. C-D) Structure of the EphA2 LBD with the bA-WLA-YSK-bio peptide (SEQ ID NO: 21) (mint green) in representations similar to A and B. (Figs. E-F) Structure of the EphA2 LBD with the bA-WLA-YRPK-bio peptide (SEQ ID NO: 27) (orange) in representations similar to A and B. The loop containing Tyr48 is observed in two different conformations.

(FIG. 5D) Comparison of dimerization curves for EphA2 WT, EphA2 L223R/L254R/V255R and G131Y in the absence (FIG. 5D) and in the presence (FIG. 5E) of YSA-GSGSK-bio (SEQ ID NO: 12). (FIG. 5F) Two-dimensional dissociation constant values ($K_{diss}$) and dimerization free energy values ($\Delta G = -RT \times \ln(10^6/K_{diss})$) calculated from the curves shown in the other panels. Shown are the best fit values and the 66% confidence intervals (standard errors). $K_{diss}$ values for all curves were compared to each other using one-way ANOVA followed by Tukey's multiple comparison test; *, P<0.05; , P<0.01; *, P<0.001; * P<0.0001; ns, not significant.

(FIG. 7A) YSA-GSGSK-bio (SEQ ID NO: 12) (dark red sticks) with polder omit map (grey mesh) contoured at 2.5s. (FIG. 7B) Detailed interactions of the biotin moiety (dark red sticks) of YSA-GSGSK-bio (SEQ ID NO: 12) with the neighboring EphA2 LBD molecule (grey sticks with transparent surface). (FIG. 7C) Ligplot representation of the biotin-EphA2 interactions. Polar interactions are indicated by dashed green lines and hydrophobic interactions by red semicircles. (FIGS. 7D-7F) Polder OMIT maps (grey mesh) of bA-WLA-Yam (SEQ ID NO: 19) (magenta sticks), bA-WLA-Yam (SEQ ID NO: 19) (mint green sticks) and bA-WLA-YRPK-bio (SEQ ID NO: 27) (orange sticks). Figure discloses SEQ ID NOS 12, 19, 21, and 27, respectively, in order of appearance.

FIG. 8 shows LigPlot diagrams detailing the interactions between YSA derivative peptides and the EphA2 LBD. All polar interactions shorter than 4 Å are indicated by dashed green lines. Peptide residues are depicted with all bonds shown and names in blue while EphA2 residues are depicted will all bonds shown and names in green, except for residues involved in hydrophobic interactions (red semicircles), whose names are in black. (FIG. 8D) Molecules B for EphA2 and D for BA-WLA-YRPK-bio (SEQ ID NO: 27) are shown.

(FIG. 9A) The main difference between the two bA-WLA-YRPK-bio (SEQ ID NO: 27) molecules in the asymmetric unit is the orientation of Arg12 and Lys14. Chain D (orange) is shown in all other figures. (FIG. 9B) The backbone of bA-WLA-YRPK-bio (SEQ ID NO: 27) appears shifted with respect to the EphA2 LBD compared to the backbone of YSA-GSGSK-bio (SEQ ID NO: 12). The additional C-terminal residues defined in bA-WLA-YRPKbio (SEQ ID NO: 27) explain its increased binding affinity. (FIGS. 9C-9D) The residues of bA-WLA-YRPK-bio (SEQ ID NO: 27) mostly overlap with those of bA-WLA-Yam (SEQ ID NO: 19) and bA-WLA-YSK-bio (SEQ ID NO: 21), except for the longer C-terminus and slight shifts in the position of the N-terminus. (FIG. 9E) The structure of 135E2 ((4-F, 3-ClPhOCH2CO) SAYPDSVPFRPam (SEQ ID NO: 8)) is very similar to that of bA-WLA-YRPK-bio (SEQ ID NO: 27) in the central portion but differs in the N- and C-termini. The proline and amidated C-terminus were not defined in the crystal structure (PDB ID 6B9L). (FIG. 9F) Detail of the C-termini highlights the different orientations of the arginine residues. All overlays were generated by superimposing the EphA2 LBD molecules, which resulted in the small shifts observed for some of the peptides.

(FIG. 10C) Cell lysate treated with YSA-GSGSK-bio (SEQ ID NO: 12) and run on the same gel for comparison. Maximal Y588 phosphorylation was similar for all biotinylated peptides, and thus the values were further normalized to the pY588 obtained with the highest peptide concentration. pAKT values were further normalized to the highest value observed without peptide or with low concentrations of peptide. The graphs show quantification of pY588 or pAKT from multiple blots (averages±SE), normalized to total EphA2 levels. The number of experiments analyzed is: 3 in FIG. 10A, 6 in FIG. 10B, 2 in FIG. 10C, 5 in FIG. 10D, 4 in FIG. 10E and 3 in FIG. 10F. For the non-biotinylated peptides (FIGS. 10G-L), pY588 and pAKT were not quantified since peptide treatment had only very small or no effects. Figure discloses SEQ ID NOS 20-21, 23-24, 27, 14, 17-19, 25, 22, and 15, respectively, in order of appearance.

(FIG. 11A) Crystallographic asymmetric unit of the YSA-GSGSK-bio-EphA2 LBD complex ("YSA-GSGSK-bio" disclosed as SEQ ID NO: 12). Two EphA2 LBD molecules form a dimer mediated by the interface containing Gly 131 (indicated as spheres) with a single biotin molecule visible near the interface. (FIG. 11B) Single bA-WLA-Yam-EphA2 complex ("bA-WLA-Yam" disclosed as SEQ ID NO: 19) (grey, in the same orientation as the grey molecule in panel A) shown with a second molecule from a different asymmetric unit cell (blue) to highlight the different interaction at the Gly 131 interface compared to all the other panels. (FIG. 11C) Crystallographic asymmetric unit of the bA-WLA-K-bio-EphA2 LBD complex (SEQ ID NO: 21). (FIG. 11D) Crystallographic asymmetric unit of the bA-WLA-YRPK-bio-EphA2 LBD complex structure ("bA-WLA-YRPK-bio" disclosed as SEQ ID NO: 27) with 1.55 Å resolution (space group P1). The inset highlights interactions and surroundings of the C-terminal carboxyl group of peptide Lys14. (FIG. 11E) Crystallographic asymmetric unit of the bA-WLA-YRPK-bio-EphA2 LBD complex structure ("bA-WLA-YRPK-bio" disclosed as SEQ ID NO: 27) with 2.50 Å resolution (space group P61). Despite the different crystal packing compared to the higher resolution structure in FIG. 11D, the same dimeric interface was formed. (FIG. 11F) Dimer of the EphA2 extracellular region in complex with ephrin-A5 (PDB ID 3MX0, ephrin-A5 omitted for clarity) showing that the same dimer interface is observed as in the four EphA2 LBD complexes with biotinylated peptides.

DETAILED DESCRIPTION OF THE INVENTION

Figure 1:
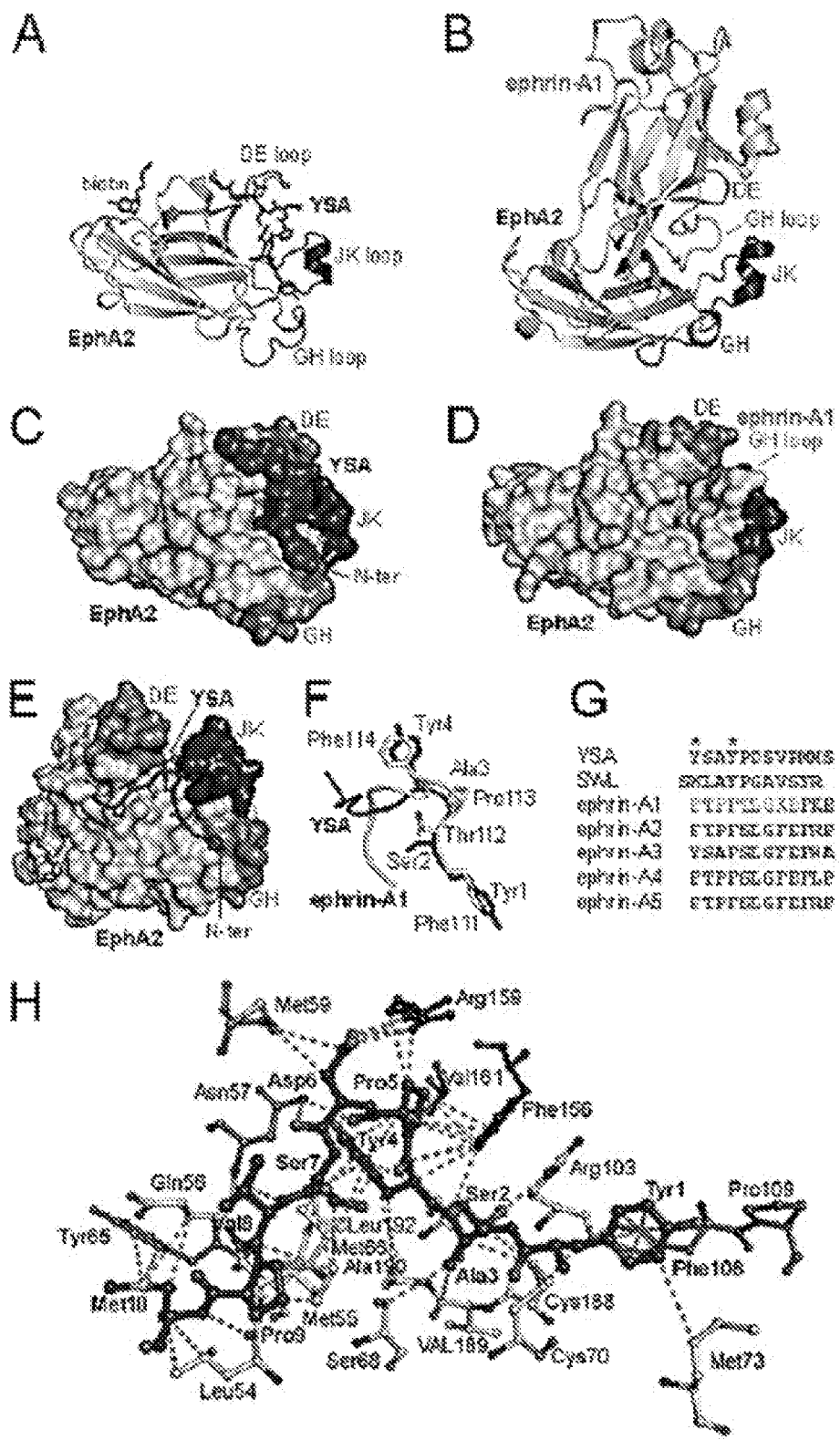
FIG. 1 shows the YSA-GSGSK-bio peptide (SEQ ID NO: 12) binds to the ephrin-binding pocket of EphA2 and mimics part of the ephrin-A1 G-H loop.

The EphA2 receptor tyrosine kinase plays an important role in a plethora of biological and disease processes, ranging from angiogenesis and cancer to inflammation and parasitic infections. EphA2 is therefore considered an important drug target. Efforts to target EphA2 and modulate its activation and downstream signaling have included different strategies. The ATP binding site in the kinase domain is suitable for targeting with small molecule inhibitors, but it is difficult to achieve specific targeting given the high conservation of this site in Eph receptors and other kinases (Barquilla and Pasquale, 2015; Boyd et al., 2014; Noberini et al., 2012). The ephrin-binding pocket in the ligand binding domain ("LBD") can also be targeted with engineered forms of the ephrin-A ligands, but these ligands bind promiscuously to all nine EphA receptors and are therefore not well-suited as selective EphA2 modulators (Barquilla and Pasquale, 2015; Boyd et al., 2014; Pasquale, 2010). The ephrin-binding pocket has also proven too large for selective high-affinity binding of small molecules (Barquilla and Pasquale, 2015; Noberini et al., 2012).

Prior to the methods and compositions described herein, the peptides known to bind to Eph receptors generally exhibited low binding affinity and low potency. Described herein are peptides which target the ephrin-binding pocket of EphA2 specifically, and mimic the binding features of the ephrin-A ligands. The peptides described herein comprise improvements including, but not limited to, low nanomolar potency.

Further, the peptides described herein comprise modifications including, but not limited to, carboxyl-terminus ("C-terminal") modifications that convert peptide derivatives from antagonists to agonists that bridge two EphA2 molecules to promote receptor autophosphorylation and downstream signaling. Also described herein are features conferring agonistic or antagonistic properties, which can be useful for different applications, and show that the peptide agonists promote EphA2 oligomerization through an unexpected bivalent binding mode.

Novel Peptides

Described herein are engineered nanomolar peptide agonists as well as antagonists that target the ephrin-binding pocket of the EphA2 receptor tyrosine kinase by using as the starting point two peptides with high specificity for EphA2 but modest (micromolar) binding affinity. Improvements guided by structural information obtained from four different peptides crystallized in complex with the EphA2 LBD have resulted in up to a surprising 350-fold increase in binding affinity. Even more surprisingly, is that this vast improvement in binding affinity was achieved with only small changes in the size of the optimized peptide agonists (from 1.99 kDa for YSA-GSGSK-bio (SEQ ID NO: 12) to 1.89 kDa for BA-WLA-YRPK-bio (SEQ ID NO: 27)) and antagonists (from 1.35 kDa for YSA to 2.0 kDa for K-bioA-WLA-YRPKam (SEQ ID NO: 32)). The sequences for exemplary peptides described herein can be found in Table 1.

The extensive network of interactions with EphA2 involving almost all the residues of BA-WLA-YRPK-bio (SEQ ID NO: 27), which is documented in the crystal structure of the peptide in complex with the EphA2 LBD, is consistent with the potency improvements observed with each additional amino acid modification in the series of engineered peptides. Interestingly, the binding of the YSA derivatives analyzed by isothermal titration calorimetry (ITC) was characterized by unusually large decreases of both entropy and enthalpy, which are most pronounced for the high affinity BA-WLA-YRPK (SEQ ID NO: 26), BA-WLA-YRPK-bio (SEQ ID NO: 27) and BA-WLA-YRPKam (SEQ ID NO: 29) peptides (Table 3). This might be expected for linear peptides that are unstructured and highly flexible in solution (resulting in an unfavorable decrease in entropy upon binding EphA2) but in which many of the residues contribute to the binding interaction with the receptor (resulting in a favorable decrease in enthalpy). The enthalpy component predominates in the best peptides that were developed, which exhibit low nanomolar affinity for EphA2. They therefore represent a marked improvement over the original peptides and their derivatives of similarly low potency that have been used by many groups over the years (Riedl and Pasquale, 2015).

Mechanism of Biotin in the Peptides Described Herein

Monomeric peptides can function as EphA2 agonists and Eph receptor activation is known to require oligomerization. Surprisingly, disclosed herein it is established that a C-terminal biotin confers the ability to efficiently promote EphA2 activation and downstream signaling in cells. Several pieces of evidence show that the likely explanation for the agonistic activity of the biotinylated peptide derivatives disclosed herein is that they function as bivalent ligands capable of bridging two EphA2 molecules. The X-ray crystal structures show distinct binding sites in the EphA2 LBD for the peptide N-terminal residues and the biotin, but do not conclusively show whether a peptide binds to two different EphA2 LBD molecules or to two binding sites within the same molecule, because of the lack of definition of the connecting residues. Nevertheless, the orientation of the biotin suggested by the shape of its electron density strongly suggests its interaction with a second EphA2 LBD molecule.

Figure 11:
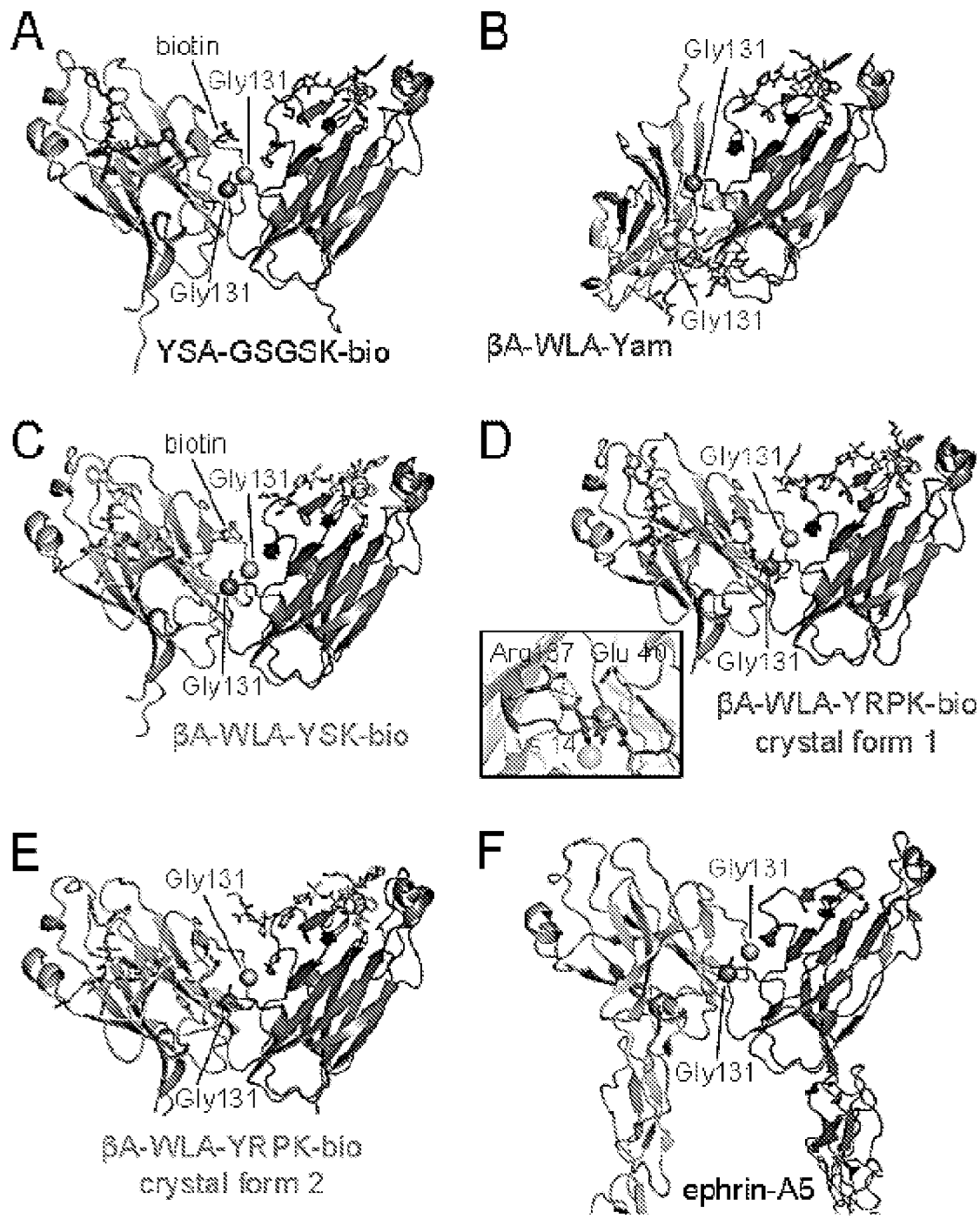
FIG. 11 shows interfaces of the different peptide-EphA2 complexes crystallized.

Although ITC measurements did not detect binding of free biotin to the EphA2 LBD, even when using high biotin concentration (1 mM; not shown), the crystal structures analyses described herein show that weak binding of the biotin moieties of two peptides to two EphA2 molecules anchored on the cell surface would be sufficient to promote receptor dimerization (FIG. 11). Supporting this model, the FRET data described herein show that the G131Y mutation, which weakens this interface, severely disrupts EphA2 oligomers induced by YSA-GSGSK-bio (SEQ ID NO: 12).

Further supporting the bivalent binding of the peptide agonists to two EphA2 molecules is the observation that the negative charge of the βA-WLA-YRPK (SEQ ID NO: 26)C-terminus interacts with a neighboring EphA2 molecule in the crystal structure. It was found that this negative charge is required for EphA2 activation in cells in the absence of the C-terminal biotin (FIGS. 4E, 4F) as well as potentiates the effects of the biotin on EphA2 activation (FIGS. 4C, 4D).

Further evidence shows that the localization of the biotin near the peptide C-terminus is critical, since an N-terminal biotin does not confer agonistic properties (FIG. 4H). The bivalent binding involving biotin is a distinctive feature of peptides targeting EphA2 because the three main EphA2 residues mediating biotin binding (Leu44, Thr45 and Tyr48), or homologous residues, are not all present in any other Eph receptor. In addition, biotinylated peptides binding to the ephrin-binding pocket of other Eph receptors do not function as agonists.

The bivalent binding mode described herein for the peptide agonists described herein is analogous to that observed for the monomeric forms of the ephrin-A ligands. Although the ephrin—As are typically anchored on the cell surface through a glycosylphosphatidylinositol linkage, they can be released by metalloproteases as soluble monomeric proteins that also activate EphA2 signaling.

Dual-Dimerization Mechanism of EphA2 Allows for Techniques to Convert Described Peptides from Agonist to Antagonist Interestingly, FRET measurements show that EphA2 can form some dimers in cells even in the absence of a bound ligand, for example when it is highly expressed in transiently transfected HEK293 cells. Furthermore, FRET analysis of the EphA2 L223R/L254R/V255R clustering interface mutant implicated this interface in the assembly of the EphA2 unliganded dimers. As described herein, destabilization of the clustering interface slightly decreases EphA2 oligomerization induced by YSA-GSGSK-bio (SEQ ID NO: 12), but to a much lesser extent than the G131Y mutation. This result indicated that the binding of peptide agonists such as YSA-GSGSK-bio (SEQ ID NO: 12) induces dimerization of EphA2 monomers through the dimerization interface but also some assembly of larger EphA2 oligomers derived from pre-existing unliganded dimers and that these oligomers would use both interfaces. In contrast, dimers induced by monomeric ephrin-Al are not affected by the EphA2 clustering interface triple mutation, demonstrating that the binding of monomeric ephrin-Al disrupts the unliganded dimers whereas the binding of the peptides does not.

While the monovalent peptides can induce weak EphA2 tyrosine phosphorylation when present at very high concentrations, or when the receptor is highly expressed by transient transfection, at lower concentrations these peptides mainly function as antagonists that inhibit EphA2 signaling by an activating ligands such as ephrin-Al Fc. Surprisingly, FRET studies have revealed that the non-biotinylated YSA-GSGSK (SEQ ID NO: 13) increases the proportion of EphA2 dimers assembled through the clustering interface.

Others have reported a series of monomeric peptide derivatives obtained through replacement of various YSA residues with unnatural amino acids or chemical moieties (Gambini et al., 2018). These YSA derivatives were presumed to be agonists, although they are not biotinylated and lack a C-terminal negative charge. However, the mechanisms described herein teach away from this conclusion. The mechanisms described herein demonstrate that the peptides described in Gambini et al. 2018 instead function as antagonists, to be used when it is desirable to inhibit rather than activate EphA2.

Figure 9:
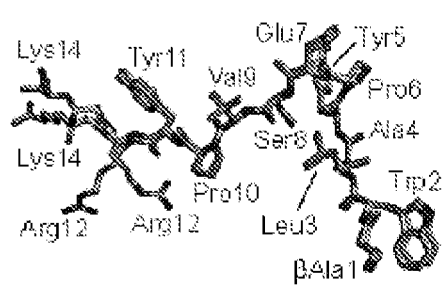
FIG. 9 shows overlays of BA-WLA-YRPK-bio (SEQ ID NO: 27) with the other peptides crystallized in complex with the EphA2 LBD.
Figure 9:
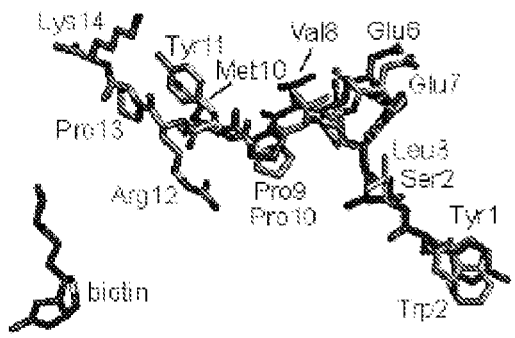
Figure 9:
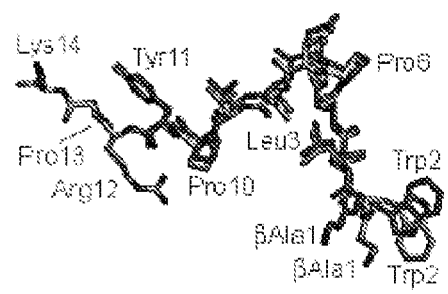
Figure 9:
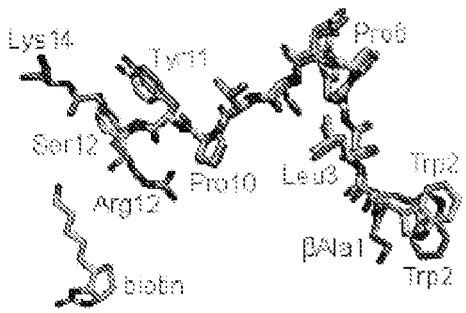
Figure 9:
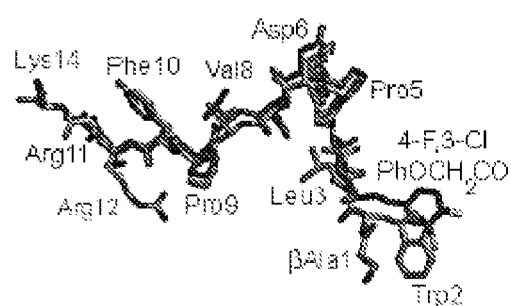
Figure 9:
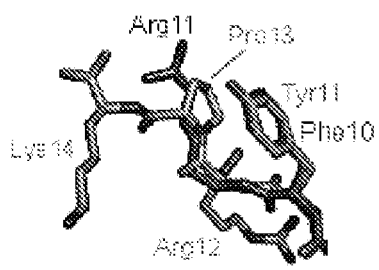

The data described herein also do not support the critical importance attributed to Arg11 in the 135E2 peptide (Gambini et al., 2018). It was found that the corresponding Arg12 in βA-WLA-YRPK-bio (SEQ ID NO: 27) interacts with Asp53 rather than Glu40, and only in one of the four molecules in the two structures described herein, while it does not make contacts with EphA2 in the other structures (FIG. 9E, 9F). Supporting the notion that the Arg does not make an important contribution to the interaction of YSA derivatives with EphA2, it is described herein that the βA-WLA-Yam (SEQ ID NO: 19) and βA-WLA-YR (SEQ ID NO: 25) peptides, which differ only in the presence of Arg12, have similar inhibitory potency in ELISAs. Furthermore, the potency of βA-WLA-YRPK-bio (SEQ ID NO: 27) is essentially unaffected by replacement of Arg12 with Ser in βA-WLA-YSPK-bio (SEQ ID NO: 28) (Table 1 and FIG. 10). Arg12, however, plays a useful role in improving peptide solubility.

Figure 7:
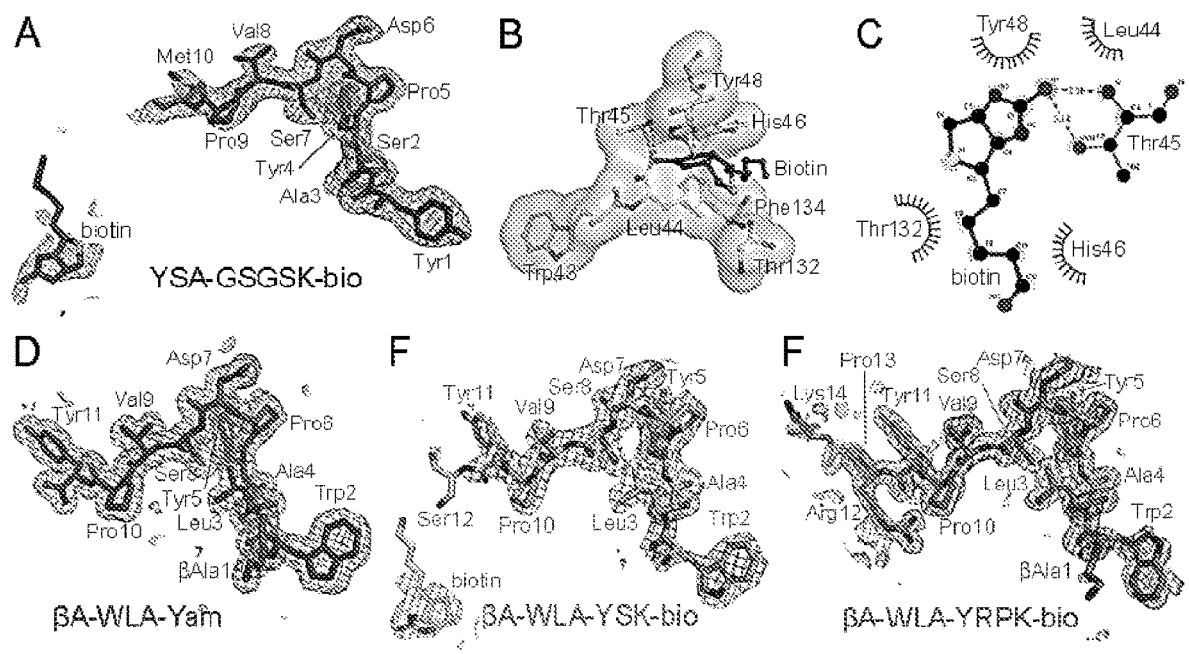
FIG. 7 shows electron density maps of YSA derivative peptides in their EphA2-bound conformation and interaction of the biotin moiety with EphA2 residues.

As a starting point to the novel modifications to the peptides described herein, the crystal structure for the complex formed by the binding of EphA2 to a known peptide (YSA) was characterized. In this initial characterization, a modified version of the peptide including a C-terminal GSGSK linker (SEQ ID NO: 4) with a biotin tag attached to the side chain of the lysine (YSA-GSGSK-bio (SEQ ID NO: 12), Table 1) was used. The crystal structure of this peptide in complex with the EphA2 LBD at a resolution of 1.9 Å is described, for the first time, herein (FIG. 1, Table 2). The structure contains two peptide-EphA2 complexes in the asymmetric unit and in both complexes the electron density is well defined for the first 10 amino acids of the peptide (FIG. 7A), indicating that this part of YSA is mainly responsible for interaction with EphA2. The peptide binds to the ephrin-binding pocket of EphA2, which is the region that also interacts with the G-H loop of ephrin-Al (FIG. 1, panels 1A, 1C, 1E versus 1B, 1D). The first 4 amino acids of YSA bound to EphA2 closely overlap with residues F111 to F114 in the G-H loop of ephrin-Al bound to the EphA2 LBD (FIG. 1F). In fact, the first 4 amino acids of YSA (YSAY (SEQ ID NO: 6)) conform to a WXXW motif (where W is an aromatic residue and X can be any residue) that is also present in the SWL peptide and the G-H loop of all the ephrin-A ligands (FIG. 1G). The remaining amino acids of YSA, however, are positioned differently from the corresponding residues of ephrin-Al (FIG. 1F). Pro5 introduces a kink in the peptide that is stabilized by a hydrogen bond with Ser7, so that the next residues occupy a groove of the EphA2 LBD that is only marginally involved in ephrin binding (FIGS. 1A, 1C, 1E versus 1B, 1D).

Figure 8A:
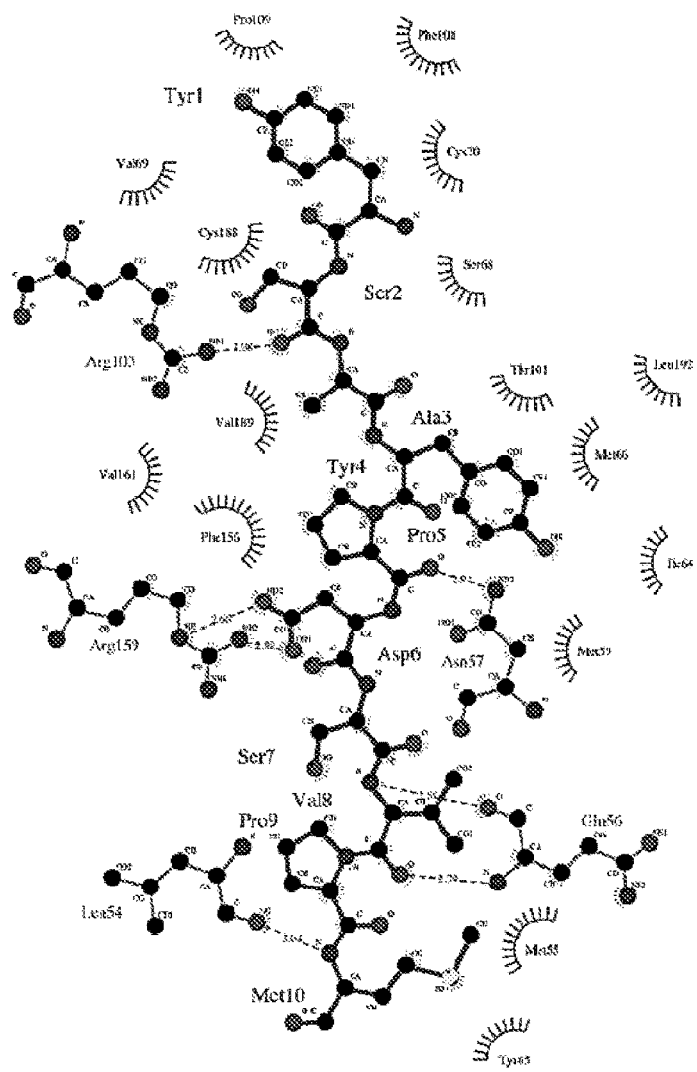
(FIG. 8A) Molecules A for EphA2 and C for YSA-GSGSK-bio (SEQ ID NO: 12) are shown (only peptide residues 1-10 are defined).

The YSA peptide forms an extensive network of hydrophobic and polar interactions with EphA2 (FIG. 1H, FIG. 8A). Key interactions involve peptide Tyrl (which binds to a hydrophobic pocket in EphA2 formed by Val72, Met73, Phe108, Pro109, and the Cys70-Cys188 disulfide bond) and Tyr4 (which is deeply buried in a hydrophobic pocket formed by Ile64, Met66, Thr101, Val161, Ala190, and Leu192). These interactions of the peptide are similar to those observed for Phe111 and Phe114 of ephrin-A1. Additional hydrophobic interactions are formed by peptide Pro5 with EphA2 Phe156 and Val161, peptide Pro9 with EphA2 Met55 and peptide Met10 with EphA2 Leu54 and Tyr65. Key polar interactions include a salt-bridge between peptide Asp6 and EphA2 Arg159 as well as hydrogen bonds between the backbone of peptide Ser2 and the side-chain of EphA2 Arg103, the backbone of peptide Pro5 and EphA2 Asn57, the backbone of peptide Val8 and the backbone of EphA2 Gln56, and the backbone of peptide Met10 with the backbone of EphA2 Leu54 (FIGS. 1H and 8A). Peptides built with Met11 and Ser12 and the GSGSK linker (SEQ ID NO: 4) in the structure were not developed because of their weak or absent electron density (FIG. 7A).

The most potent peptides described herein also have good solubility in aqueous solutions. The peptides described herein have the highest binding affinity among the EphA2-targeting peptides reported to date, by a surprisingly, significant amount. In addition, dimerization and immobilization on the surface of nanoparticles can further increase EphA2 targeting potency through avidity effects, as well as confer or potentiate agonistic properties. Disclosed herein are methods of dimerization and immobilization on the surface of nanoparticles to increase EphA2 targeting potency through avidity effects. The peptides described herein represent a valuable resource to modulate EphA2 by enabling potent and selective modification of the function of this receptor to increase or decrease signaling and to prevent binding of infectious agents.

The peptides described above are generally used to reduce inflammation. The peptides exert anti-inflammatory and also, immune-modulating effects. The peptides described herein can also be used to treat, prevent, or improve the symptoms of several other pathologies like cancer, autoimmune tissue destruction, and hyperglycemia.

The term "derivative" as used herein refers to peptides which have been chemically modified, including, but not limited to, by techniques such as biotinylation, ubiquitination, labeling, pegylation, glycosylation, or addition of other molecules. A molecule is also a "derivative" of another molecule when it contains additional chemical moieties not normally a part of the molecule. Such moieties can improve the molecule's solubility, absorption, biological half-life, etc. The moieties can alternatively decrease the toxicity of the molecule, eliminate or attenuate any undesirable side effect of the molecule, etc. Additional chemical moieties not normally a part of the molecule can increase the potency or binding affinity of said molecule.

Thus, in some embodiments, the peptides and methods disclosed herein comprise peptide derivatives, such as biotinylated peptides.

Formulations of Therapeutically Effective Compositions of Peptides Described Herein The administration of one or more peptides as disclosed herein or a mutant, variant, analog or derivative thereof may be by any suitable means that results in a concentration of the protein that treats the disorder. The compound may be contained in any appropriate amount in any suitable carrier substance, and is generally present in an amount of 1-95% by weight of the total weight of the composition. The composition may be provided in a dosage form that is suitable for the oral, parenteral (e.g., intravenously or intramuscularly), intraperitoneal, rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols. The pharmaceutical compositions may be formulated according to conventional pharmaceutical practice (see, e.g., Remington: The Science and Practice of Pharmacy, 20th edition, 2000, ed. A. R. Gennaro, Lippincott Williams & Wilkins, Philadelphia, and Encyclopedia of Pharmaceutical Technology, eds. J. Swarbrick and J. C. Boylan, 1988-1999, Marcel Dekker, New York, incorporated, herein, by reference in its entirety).

Pharmaceutical compositions according to the methods and compositions described herein may be formulated to release the active compound immediately upon administration or at any predetermined time or time period after administration. The latter types of compositions are generally known as controlled release formulations, which include (i) formulations that create substantially constant concentrations of the agent(s) of the compositions described herein within the body over an extended period of time; (ii) formulations that after a predetermined lag time create substantially constant concentrations of the agent(s) of the compositions described herein within the body over an extended period of time; (iii) formulations that sustain the agent(s) action during a predetermined time period by maintaining a relatively constant, effective level of the agent(s) in the body with concomitant minimization of undesirable side effects associated with fluctuations in the plasma level of the agent(s); (iv) formulations that localize action of agent(s), e.g., spatial placement of a controlled release composition adjacent to or in the diseased tissue or organ; (v) formulations that achieve convenience of dosing, e.g., administering the composition once per week or once every two weeks; and (vi) formulations that target the action of the agent(s) by using carriers or chemical derivatives to deliver the therapeutic to a particular target cell type. Administration of the protein in the form of a controlled release formulation is especially preferred for compounds having a narrow absorption window in the gastrointestinal tract or a relatively short biological half-life.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the protein is formulated with appropriate excipients into a pharmaceutical composition that, upon administration, releases the protein in a controlled manner. Examples include single or multiple unit tablet or capsule compositions, oil solutions, suspensions, emulsions, microcapsules, molecular complexes, microspheres, nanoparticles, patches, and liposomes.

As used herein, the phrases "parenteral administration" and "administered parenterally" as used herein mean modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebrospinal, and intrastemal injection and infusion. The phrases "systemic administration," "administered systemically", "peripheral administration" and "administered peripherally" as used herein mean the administration therapeutic compositions other than directly into a tumor such that it enters the subject's system and, thus, is subject to metabolism and other like processes.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent or encapsulating material, involved in maintaining the activity of or carrying or transporting the subject agents from one organ, or portion of the body, to another organ, or portion of the body. In addition to being "pharmaceutically acceptable" as that term is defined herein, each carrier must also be "acceptable" in the sense of being compatible with the other ingredients of the formulation. The pharmaceutical formulation comprising the one or more peptides as disclosed herein or a mutant, variant, analog or derivative thereof in combination with one or more pharmaceutically acceptable ingredients. The carrier can be in the form of a solid, semi-solid or liquid diluent, cream or a capsule. These pharmaceutical preparations are a further object of the methods and compositions described herein. Usually the amount of active compounds is between 0.1-95% by weight of the preparation, preferably between 0.2-20% by weight in preparations for parenteral use and preferably between 1 and 50% by weight in preparations for oral administration. For the clinical use of the methods described herein, targeted delivery compositions are formulated into pharmaceutical compositions or pharmaceutical formulations for parenteral administration, e.g., intravenous; mucosal, e.g., intranasal; enteral, e.g., oral; topical, e.g., transdermal; ocular, e.g., via corneal scarification or other mode of administration. The pharmaceutical composition contains a compound of the methods and compositions described herein in combination with one or more pharmaceutically acceptable ingredients. The carrier can be in the form of a solid, semi-solid or liquid diluent, cream or a capsule.

The term "pharmaceutically acceptable carriers" is intended to include all solvents, diluents, or other liquid vehicle, dispersion or suspension aids, surface active agents, isotonic agents, thickening or emulsifying agents, preservatives, solid binders, lubricants and the like, as suited to the particular dosage form desired. Typically, such compounds are carried or transported from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its functional derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Parenteral Compositions

The pharmaceutical composition may be administered parenterally by injection, infusion, or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation or it may be presented as a dry powder to be reconstituted with water or another suitable vehicle before use. Apart from the active agent(s), the composition may include suitable parenterally acceptable carriers and/or excipients. The active agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing agents.

As indicated above, the pharmaceutical compositions according to the methods and compositions described herein may be in a form suitable for sterile injection. To prepare such a composition, the suitable active agent(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, dextrose solution, and isotonic sodium chloride solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfate, sodium sulfite and the like; oil-soluble anti-oxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present compositions described herein include those suitable for intravenous, oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect.

Methods of preparing these formulations or compositions include the step of bringing into association a compound of the compositions described herein with the carrier and, optionally, one or more accessory ingredients. In general, the formulations are prepared by uniformly and intimately bringing into association a compound of the compositions described herein with liquid carriers, or finely divided solid carriers, or both, and then, if necessary, shaping the product.

Formulations of the compositions described herein suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present compositions described herein as an active ingredient. A compound of the present compositions described herein may also be administered as a bolus, electuary or paste.

Pharmaceutical compositions of the compositions described herein are suitable for parenteral administration comprise one or more peptides as disclosed herein or a mutant, variant, analog or derivative thereof in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions comprising one or more peptides as disclosed herein or a mutant, variant, analog or derivative thereof include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents and dispersing agents. Prevention of the action of microorganisms may be ensured by the inclusion of various antibacterial and antifungal agents, including, but not limited to, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly (anhydrides). Injectable formulations are also prepared by entrapping the drug, such as one or more peptides as disclosed herein or a mutant, variant, analog or derivative thereof in liposomes or microemulsions which are compatible with body tissue.

Regardless of the route of administration selected, the compounds of the present compositions described herein, which may be used in a suitable hydrated form, and/or the pharmaceutical compositions of the present compositions described herein, are formulated into pharmaceutically acceptable dosage forms by conventional methods known to those of ordinary skill in the art.

Controlled Release Parenteral Compositions

Controlled release parenteral compositions may be in form of aqueous suspensions, microspheres, microcapsules, magnetic microspheres, oil solutions, oil suspensions, or emulsions. The composition may also be incorporated in biocompatible carriers, liposomes, nanoparticles, implants, or infusion devices.

Materials for use in the preparation of micro-spheres and/or microcapsules are, e.g., biodegradable/bio-erodible polymers such as polygalactia poly-(isobutyl cya-noacrylate), poly (2-hydroxyethyl-L-glutamine), poly (lactic acid), polyglycolic acid, and mixtures thereof. Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly (caprolactone), poly (lactic acid), poly (glycolic acid) or poly (ortho esters)) or combinations thereof.

Solid Dosage Forms for Oral Use

Formulations for oral use include tablets containing the active ingredient(s) in a mixture with non-toxic pharmaceutically acceptable excipients, and such formulations are known to the skilled artisan.

These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and anti-adhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the protein in a predetermined pattern (e.g., in order to achieve a controlled release formulation) or it may be adapted not to release the agent(s) until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material such as, e.g., glyceryl monostearate or glyceryl distearate, may be employed.

The solid tablet compositions may include a coating adapted to protect the composition from unwanted chemical changes, (e.g., chemical degradation prior to the release of the active substances). The coating may be applied on the solid dosage form in a similar manner as that described in Encyclopedia of Pharmaceutical Technology, supra.

The compositions described herein may be mixed together in the tablet, or may be partitioned. In one example, a first agent is contained on the inside of the tablet, and a second agent is on the outside, such that a substantial portion of the second agent is released prior to the release of the first agent.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate, or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus, or spray drying equipment.

In solid dosage forms of the compositions described herein for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present compositions described herein, such as dragees, capsules, pills and granules, may optionally be scored or prepared with coatings and shells, such as enteric coatings and other coatings well known in the art of pharmacy. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally be of a composition that releases the active ingredient(s) only, or preferentially, in a certain portion of the gastrointestinal tract, optionally, in a delayed manner. Examples of embed-ding compositions which can be used include polymeric substances and waxes. The active ingredient can also be in micro-encapsulated form, if appropriate, with one or more of the above-described excipients. In one aspect, a solution of resolvin and/or protectin or precursor or analog thereof can be administered as eye drops for ocular neovascularization or ear drops to treat otitis.

Liquid dosage forms for oral administration of the compounds of the compositions described herein include pharmaceutically acceptable emulsions, microemulsions, solutions, suspensions, syrups and elixirs.

In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration of one or more peptides as disclosed herein or derivative thereof include, but are not limited to, powders, sprays, ointments, pastes, creams, lotions, gels, solutions, patches and inhalants. The active compound may be mixed under sterile conditions with a pharmaceutically acceptable carrier, and with any preservatives, buffers, or propellants, which may be required.

The ointments, pastes, creams and gels may contain, in addition to an active compound of the compositions described herein, excipients, including, but not limited to, animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to a compound of the compositions described herein, excipients such as lactose, talc, silicic acid, aluminum hydroxide, calcium silicates and polyamide powder, or combinations thereof. Sprays can additionally contain customary propellants, such as chlorofluorohydrocarbons and volatile unsubstituted hydrocarbons, such as butane and propane.

Transdermal patches have the added advantage of providing controlled delivery of the compounds (resolvins and/or protectins and/or precursors or analogues thereof) of the present compositions described herein to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel. In another aspect, biodegradable or absorbable polymers can provide extended, often localized, release of polypeptide agents. The potential benefits of an increased half-life or extended release for a therapeutic agent are clear. A potential benefit of localized release is the ability to achieve much higher localized dosages or concentrations, for greater lengths of time, relative to broader systemic administration, with the potential to also avoid possible undesirable side effects that may occur with systemic administration.

Bioabsorbable polymeric matrix suitable for delivery of the one or more peptides as disclosed herein or a mutant, variant, analog or derivative thereof can be selected from a variety of synthetic bioabsorbable polymers, which are described extensively in the literature. Such synthetic bioabsorbable, biocompatible polymers, which may release proteins over several weeks or months can include, for example, poly-a-hydroxy acids (e.g. polylactides, polyglycolides and their copolymers), polyanhydrides, polyorthoesters, segmented block copolymers of polyethylene glycol and polybutylene terephtalate (Polyactive™), tyrosine derivative polymers or poly (ester-amides). Suitable bioabsorbable polymers to be used in manufacturing of drug delivery materials and implants have been previously described. The particular bioabsorbable polymer that should be selected will depend upon the particular patient that is being treated.

Dosages

With respect to the therapeutic methods described herein, it is not intended that the administration of the one or more peptides as disclosed herein, or a derivative thereof, and be limited to a particular mode of administration, dosage, or frequency of dosing; the present methods and compositions described herein contemplate all modes of administration, including intramuscular, intravenous, intraperitoneal, intravesicular, intraarticular, intralesional, subcutaneous, or any other route sufficient to provide a dose adequate to treat the inflammation-related disorder. The therapeutic may be administered to the patient in a single dose or in multiple doses. When multiple doses are administered, the doses may be separated from one another by, for example, one hour, three hours, six hours, eight hours, one day, two days, one week, two weeks, or one month. For example, the therapeutic may be administered for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the compositions. For example, the dosage of the therapeutic can be increased if the lower dose does not provide sufficient therapeutic activity.

While the attending physician ultimately will decide the appropriate amount and dosage regimen, therapeutically effective amounts of the one or more peptides as disclosed herein or a mutant, variant, analog or derivative thereof may be provided at a dose of 0.0001, 0.001, 0.01 0.1, 1, 5, 10, 25, 50, 100, 500, or 1,000 mg/kg. Effective doses may be extrapolated from dose-response curves derived from in vitro or animal model test bioassays or systems.

Dosages for a particular patient or subject can be determined by one of ordinary skill in the art using conventional considerations. A physician may, for example, prescribe a relatively low dose at first, subsequently increasing the dose until an appropriate response is obtained. The dose administered to a patient is sufficient to effect a beneficial therapeutic response in the patient over time, or, e.g., to reduce symptoms, or other appropriate activity, depending on the application. The dose is determined by the efficacy of the particular formulation, and the activity, stability or serum half-life of the one or more peptides as disclosed herein or a mutant, variant, analog or derivative thereof and the condition of the patient, as well as the body weight or surface area of the patient to be treated. The size of the dose is also determined by the existence, nature, and extent of any adverse side-effects that accompany the administration of a particular vector, formulation, or the like in a particular subject. Therapeutic compositions comprising one or more peptides as disclosed herein, or a derivative thereof, are optionally tested in one or more appropriate in vitro and/or in vivo animal models of disease, such as models of cancer or inflammation, to confirm efficacy, tissue metabolism, and to estimate dosages. In particular, dosages can be initially determined by activity, stability or other suitable measures of treatment vs. non-treatment (e.g., comparison of treated vs. untreated cells or animal models), in a relevant assay. Formulations are administered at a rate determined by the LD50 of the relevant formulation, and/or observation of any side-effects of one or more peptides as disclosed herein or a mutant, variant, analog or derivative thereof. Administration can be accomplished via single or divided doses.

In determining the effective amount of one or more peptides as disclosed herein or a mutant, variant, analog or derivative thereof to be administered in the treatment or prophylaxis of disease the physician evaluates circulating plasma levels, formulation toxicities, and progression of the disease.

The efficacy and toxicity of the compound can be determined by standard pharmaceutical procedures in cell cultures or experimental animals, e.g., ED50 (the dose is effective in 50% of the population) and LD50 (the dose is lethal to 50% of the population). The dose ratio of toxic to therapeutic effects is the therapeutic index, and it can be expressed as the ratio, LD50/ED50. Pharmaceutical compositions which exhibit large therapeutic indices are preferred.

These compounds may be administered to humans and other animals for therapy by any suitable route of administration that works for small peptides, including orally, nasally, as by, for example, a spray, rectally, intravaginally, parenterally, intracisternally and topically, as by powders, ointments or drops, including buccally and sub-lingually.

Actual dosage levels of the active ingredients in the pharmaceutical compositions of compositions described herein may be varied so as to obtain an amount of the active ingredient which is effective to achieve the desired therapeutic response for a particular subject, composition, and mode of administration, without being toxic to the subject.

The selected dosage level will depend upon a variety of factors including the activity of the particular compound of the present compositions described herein employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

Gene Therapy

One or more peptides as disclosed herein or derivative thereof can be effectively used in treatment by gene therapy. The general principle is to introduce the polynucleotide into a target cell in a patient.

Entry into the cell is facilitated by suitable techniques known in the art such as providing the polynucleotide in the form of a suitable vector, or encapsulation of the polynucleotide in a liposome.

A desired mode of gene therapy is to provide the polynucleotide in such a way that it will replicate inside the cell, enhancing and prolonging the desired effect. Thus, the polynucleotide is operably linked to a suitable promoter, such as the natural promoter of the corresponding gene, a heterologous promoter that is intrinsically active in liver, neuronal, bone, muscle, skin, joint, or cartilage cells, or a heterologous promoter that can be induced by a suitable agent.

Expression vectors compatible with eukaryotic cells, preferably those compatible with vertebrate cells, can be used to produce recombinant constructs for the expression of one or more peptides as disclosed herein or a mutant, variant, analog or derivative thereof, including fusion proteins with one or more peptides as disclosed herein or a mutant, variant, analog or derivative thereof. Eukaryotic cell expression vectors are well known in the art and are available from several commercial sources. Typically, such vectors are provided containing convenient restriction sites for insertion of the desired DNA segment. These vectors can be viral vectors such as adenovirus, adeno-associated virus, pox virus such as an orthopox (vaccinia and attenuated vaccinia), avipox, lentivirus, murine maloney leukemia virus, etc. Alternatively, plasmid expression vectors can be used.

Viral vector systems which can be utilized in the present methods and compositions described herein include, but are not limited to, (a) adenovirus vectors; (b) retrovirus vectors; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and G) a helper-dependent or gutless adenovirus.

The vector may or may not be incorporated into the cells genome. The constructs may include viral sequences for transfection, if desired. Alternatively, the construct may be incorporated into vectors capable of episomal replication, e.g. EPV and EBV vectors.

By "operably linked" is meant that a nucleic acid molecule and one or more regulatory sequences (e.g., a promoter) are connected in such a way as to permit expression and/or secretion of the peptide of the nucleic acid molecule when the appropriate molecules (e.g., transcriptional activator proteins) are bound to the regulatory sequences. Stated another way, the term "operatively linked" as used herein refers to the functional relationship of the nucleic acid sequences with regulatory sequences of nucleotides, such as promoters, enhancers, transcriptional and translational stop sites, and other signal sequences. For example, operative linkage of nucleic acid sequences, typically DNA, to a regulatory sequence or promoter region refers to the physical and functional relationship between the DNA and the regulatory sequence or promoter such that the transcription of such DNA is initiated from the regulatory sequence or promoter, by an RNA polymerase that specifically recognizes, binds and transcribes the DNA. In order to optimize expression and/or in vitro transcription, it may be necessary to modify the regulatory sequence for the expression of the nucleic acid or DNA in the cell type for which it is expressed. The desirability of, or need of, such modification may be empirically determined. An operatively linked polynucleotide which is to be expressed typically includes an appropriate start signal (e.g., ATG) and maintains the correct reading frame to permit expression of the polynucleotide sequence under the control of the expression control sequence, and production of the desired polypeptide encoded by the polynucleotide sequence.

As used herein, the terms "promoter" or "promoter region" or "promoter element" have been defined herein, refers to a segment of a nucleic acid sequence, typically but not limited to DNA or RNA or analogues thereof, that controls the transcription of the nucleic acid sequence to which it is operatively linked. The promoter region includes specific sequences that are sufficient for RNA polymerase recognition, binding and transcription initiation. This portion of the promoter region is referred to as the promoter. In addition, the promoter region includes sequences which modulate this recognition, binding and transcription initiation activity of RNA polymerase. These sequences may be ds-acting or may be responsive to trans-acting factors. Promoters, depending upon the nature of the regulation may be constitutive or regulated.

The term "regulatory sequences" is used inter-changeably with "regulatory elements" herein refers element to a segment of nucleic acid, typically but not limited to DNA or RNA or analogues thereof, that modulates the transcription of the nucleic acid sequence to which it is operatively linked, and thus act as transcriptional modulators. Regulatory sequences modulate the expression of gene and/or nucleic acid sequence to which they are operatively linked. Regulatory sequence often comprise "regulatory elements" which are nucleic acid sequences that are transcription binding domains and are recognized by the nucleic acid-binding domains of transcriptional proteins and/or transcription factors, repressors or enhancers etc. Typical regulatory sequences include, but are not limited to, transcriptional promoters, inducible promoters and transcriptional elements, an optional operate sequence to control transcription, a sequence encoding suitable mRNA ribosomal binding sites, and sequences to control the termination of transcription and/or translation. Included in the term "regulatory elements" are nucleic acid sequences such as initiation signals, enhancers, and promoters, which induce or control transcription of protein coding sequences with which they are operatively linked. In some examples, transcription of a recombinant gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of a protein. In some instances the promoter sequence is recognized by the synthetic machinery of the cell, or introduced synthetic machinery, required for initiating transcription of a specific gene.

Regulatory sequences can be a single regulatory sequence or multiple regulatory sequences, or modified regulatory sequences or fragments thereof. Modified regulatory sequences are regulatory sequences where the nucleic acid sequence has been changed or modified by some means, including, but not limited to, mutation, methylation etc.

In some embodiments, it can be advantageous to direct expression of one or more peptides as disclosed herein or a mutant, variant, analog or derivative thereof in a tissue- or cell-specific manner.

A gene or nucleic acid sequence can be introduced into a target cell by any suitable method. For example, one or more peptides as disclosed herein, or a derivative thereof, constructs can be introduced into a cell by transfection (e.g., calcium phosphate or DEAE-dextran mediated transfection), lipofection, electroporation, microinjection (e.g., by direct injection of naked DNA), biolistics, infection with a viral vector containing a muscle related transgene, cell fusion, chromosome-mediated gene transfer, microcell-mediated gene transfer, nuclear transfer, and the like. A nucleic acid encoding one or more peptides as disclosed herein, or a derivative thereof, can be introduced into cells by electroporation.

In certain embodiments, a gene or nucleic acid sequence encoding one or more peptides as disclosed herein or a mutant, variant, analog or derivative thereof can be introduced into target cells by transfection or lipofection. Suitable agents for transfection or lipofection include, for example, calcium phosphate, DEAE dextran, lipofectin, lipfectamine, DIMRIE C, Superfect, and Effectin (Qiagen), unifectin, maxifectin, DOTMA, DOGS (Transfectam; dioctadecylamidoglycylspermine), DOPE (1,2-dioleoyl-sn-glycero-3-phosphoethanolamine), DOTAP (1,2-dioleoyl-3-trimethylammonium propane), DDAB (dimethyl dioctadecylammonium bromide), DHDEAB (N,N-di-n-hexadecyl-N,N-dihydroxyethyl ammonium bromide), HDEAB (N-n-hexadecyl-N,N-dihydroxyethylammonium bromide), polybrene, poly (ethylenimine) (PEI), and the like.

Methods known in the art for the therapeutic delivery of agents such as proteins and/or nucleic acids can be used for the delivery of a peptide or nucleic acid encoding one or more peptides as disclosed herein or a derivative thereof, e.g., cellular transfection, gene therapy, direct administration with a delivery vehicle or pharmaceutically acceptable carrier, indirect delivery by providing recombinant cells comprising a nucleic acid encoding a targeting fusion polypeptide of the compositions described herein.

Various delivery systems are known and can be used to directly administer therapeutic peptides as disclosed herein, or a derivative thereof, and/or a nucleic acid encoding one or more peptides as disclosed herein, or derivative thereof, e.g., encapsulation in liposomes, microparticles, microcapsules, recombinant cells capable of expressing the compound, and receptor-mediated endocytosis (see, e.g., Wu and Wu, 1987, J. Bioi. Chem. 262:4429-4432). Methods of introduction can be enteral or parenteral and include but are not limited to intradermal, intramuscular, intraperitoneal, intravenous, subcutaneous, pulmonary, intranasal, intraocular, epidural, and oral routes. The agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the pharmaceutical compositions of the compositions described herein locally to the area in need of treatment; this may be achieved, for example, and not by way of limitation, by local infusion during surgery, topical application, e.g., by injection, by means of a catheter, or by means of an implant, the implant being of a porous, non-porous, or gelatinous material, including membranes, such as sialastic membranes, fibers, or commercial skin substitutes.

In another embodiment, the active agent can be delivered in a vesicle, in particular a liposome. In yet another embodiment, the active agent can be delivered in a controlled release system. In one embodiment, a pump may be used. In another embodiment, polymeric materials can be used.

Thus, a wide variety of gene transfer/gene therapy vectors and constructs are known in the art. These vectors are readily adapted for use in the methods described herein. By the appropriate manipulation using recombinant DNA/molecular biology techniques to insert an operatively linked polypeptide encoding nucleic acid segment into the selected expression/delivery vector, many equivalent vectors for the practice of the methods described herein can be generated.

OTHER EMBODIMENTS

From the foregoing description, it will be apparent that variations and modifications may be made to the methods and compositions described herein to adopt it to various usages and conditions. Such embodiments are also within the scope of the following claims.

The disclosure also contemplates an article of manufacture, which is a labeled container for providing the one or more peptides as disclosed herein, or a mutant, variant, analog or derivative thereof. An article of manufacture comprises packaging material and a pharmaceutical agent of the one or more peptides as disclosed herein, or a derivative thereof, contained within the packaging material.

The pharmaceutical agent in an article of manufacture is any of the compositions described herein suitable for providing the one or more peptides as disclosed herein or a mutant, variant, analog or derivative thereof and formulated into a pharmaceutically acceptable form as described herein according to the disclosed indications. Thus, the composition can comprise the one or more peptides as disclosed herein, or a derivative thereof, or a DNA molecule which is capable of expressing such a peptide.

The article of manufacture contains an amount of pharmaceutical agent sufficient for use in treating a condition indicated herein, either in unit or multiple dosages. The packaging material comprises a label which indicates the use of the pharmaceutical agent contained therein.

The label can further include instructions for use and related information as may be required for marketing. The packaging material can include container(s) for storage of the pharmaceutical agent.

As used herein, the term packaging material refers to a material such as glass, plastic, paper, foil, and the like capable of holding within fixed means a pharmaceutical agent. Thus, for example, the packaging material can be plastic or glass vials, laminated envelopes and the like containers used to contain a pharmaceutical composition including the pharmaceutical agent.

In preferred embodiments, the packaging material includes a label that is a tangible expression describing the contents of the article of manufacture and the use of the pharmaceutical agent contained therein.

EXAMPLES

The following examples are provided to better illustrate the claimed methods and compositions and are not to be interpreted as limiting the scope of the methods and compositions described herein. To the extent that specific materials are mentioned, it is merely for purposes of illustration and is not intended to limit the methods and compositions described herein. One skilled in the art may develop equivalent means or reactants without the exercise of inventive capacity and without departing from the scope of the methods and compositions described herein.

Example 1: Making Peptide Derivatives

Peptides

Peptide identity and purity were documented by mass spectrometry and high-performance liquid chromatography (HPLC) (Table 4). The peptide solubility values reported in Table 1 were determined. Concentrated peptide stocks were prepared in DMSO or $H_2O$ and stored frozen at −80° C.

EphA2 Ligand Binding Doman ("LBD") Expression and Purification

EphA2 receptors were expressed and purified. The DNA sequence coding for the EphA2 LBD (residues 28-200) with an additional C-terminal Ala-6xHis-tag sequence (SEQ ID NO: 9) was cloned into a modified version of a pETNKI-LIC vector that encodes a N-terminal MASQGPG sequence (SEQ ID NO: 10) in a pET29 vector backbone. The EphA2 LBD was expressed in E. coli Origami 2 (DE3) (Novagen) grown in 2xYT medium (BD Difco) at 20° C. overnight and purified using Ni-NTA agarose (Qiagen) followed by size-exclusion chromatography on a Superdex 75 10/300 GL column (GE Healthcare) equilibrated in 100 mM NaCl, 10 mM HEPES pH 7.9. The EphA2 LBD was concentrated to 5-7 mg/ml, flash frozen in aliquots, and stored at −80° C.

Crystallization and Structure Solution

Figure 8B:
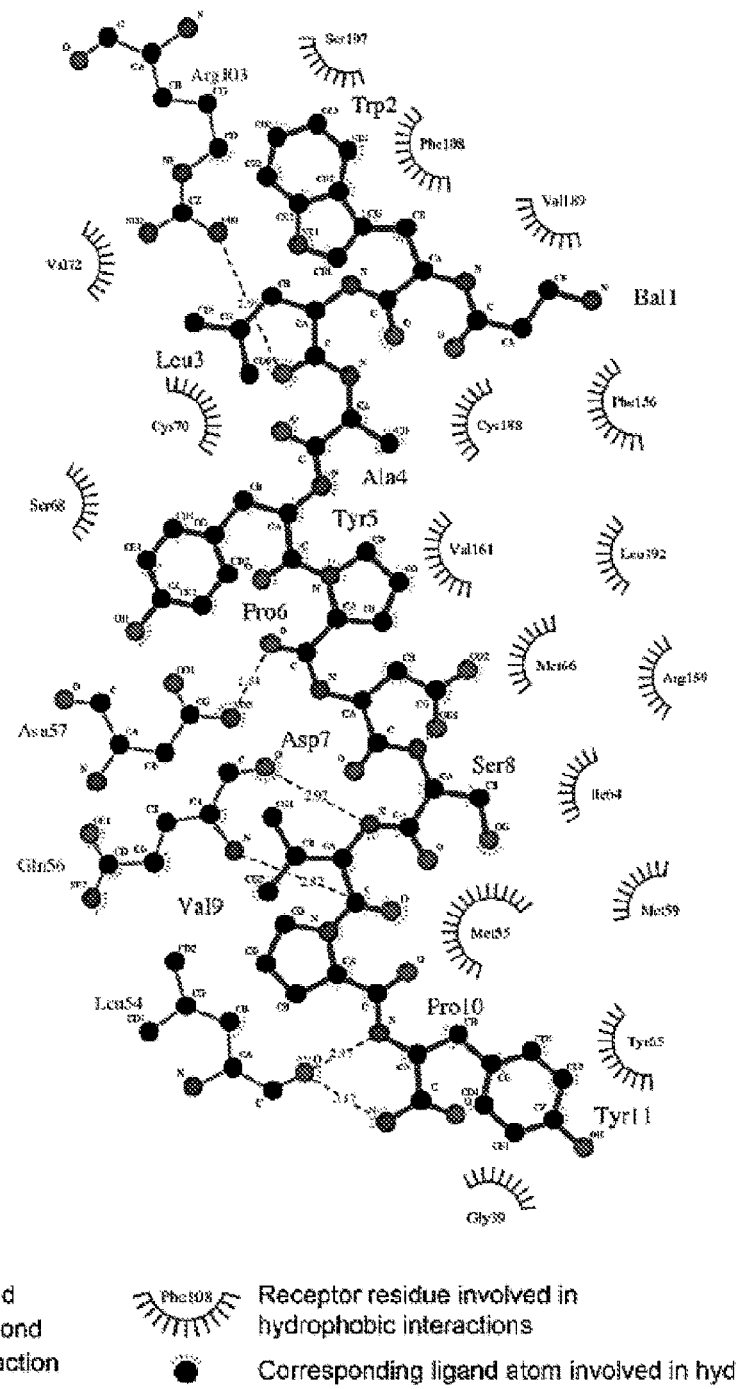
(FIG. 8B) Molecules B for EphA2 and D for BA-WLA-Yam (SEQ ID NO: 19) are shown.
Figure 8C:
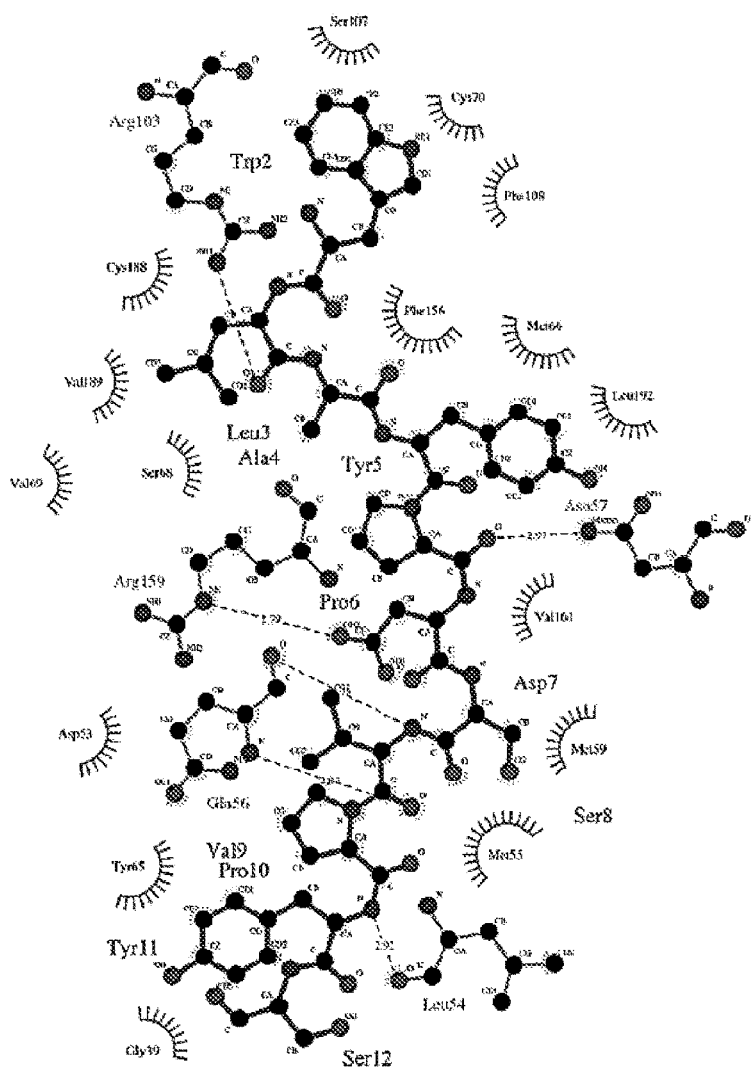
(FIG. 8C) Molecules A for EphA2 and C for BA-WLA-YSK-bio (SEQ ID NO: 21) are shown.

EphA2 LBD (7 mg ml-1) was mixed with a 2-fold molar excess of YSA-GSGSK-bio peptide (SEQ ID NO: 12) dissolved to 2.9 mM in water, and initial crystals were obtained with the Hampton Index HT screen. Crystals were optimized with the Hampton Additive Screen HT, changes in the ratio of protein to precipitate volume, and by two rounds of crush seeding. Final crystals for structure solution were obtained by mixing 2.8 µl protein solution with 1 µl reservoir solution (0.09 M BIS-TRIS pH 5.5, 22.5% w/v PEG 3,350, 3% w/v 6-aminohexanoic acid) and equilibration against 50 µl reservoir solution at 20° C. in sitting-drop MRC 48-well plates (Molecular Dimensions). Clusters of plate-shaped crystals appeared overnight. Crystals were cryoprotected by step-wise transfer to reservoir solutions with 5-15% glycerol and cryo-cooled in a nitrogen stream at 100 K. Diffraction data were collected on a rotating anode X-ray generator (Rigaku FR-E) at 100 K and processed in XDS and with software from the CCP4 suite. Phases were obtained using molecular replacement in Phaser with chain A of PDB ID 3HEI (Himanen et al., 2009) as search model. Model building and refinement were respectively performed in Coot (Emsley et al., 2010) or Refmac (Murshudov et al., 2011) and Phenix (Adams et al., 2010). The final model was validated using MolProbity (Chen et al., 2010). Data collection and refinement statistics are reported in Table 2. All structural figures were generated using PyMOL (Schrodinger, LLC). Peptide Polder OMIT electron density maps in FIG. 7 were generated according to Liebschner et al., 2017 and the LigPlot peptide-EphA2 interaction diagrams in FIG. 8 were generated according to Laskowski and Swindells, 2011.

Crystals for two of the other four EphA2/peptide complexes were grown in the same conditions, whereas the two structures of the EphA2/bA-WLA-YRPK-bio complex (SEQ ID NO: 27) formed in a similar condition with 0.09 M Sodium-Acetate pH 4.5, instead of Bis-Tris pH5.5. (Table 2). The protein-to-precipitant drop ratio was in the range of 1.8-2.6 µl protein to 1 µl precipitant for these crystals. Despite these similarities, the different complexes crystallized in different space groups (Table 2), each with two EphA2/peptide complexes in the asymmetric unit.

Isothermal Titration Calorimetry (ITC)

For ITC, all peptides were dissolved in DMSO and both the EphA2 LBD and the peptides were diluted to obtain a final buffer containing 9.5 mM HEPES, pH 7.9, 95 mM NaCl, and 5% DMSO. The experiments were carried out at 296 K (23° C.) using an ITC200 calorimeter (Microcal). Two-microliter aliquots of a peptide solution were injected into the cell containing 205 µL EphA2 LBD. 200-400 µM peptides were titrated into 20-40 µM EphA2 LBD. Experimental data were analyzed using the Origin software package (Microcal). The integrated values for the reaction heats were normalized to the amount of injected peptide after blank subtraction.

Example 2: Modifications Increasing the Potency of YSA Derivatives

Figure 2:
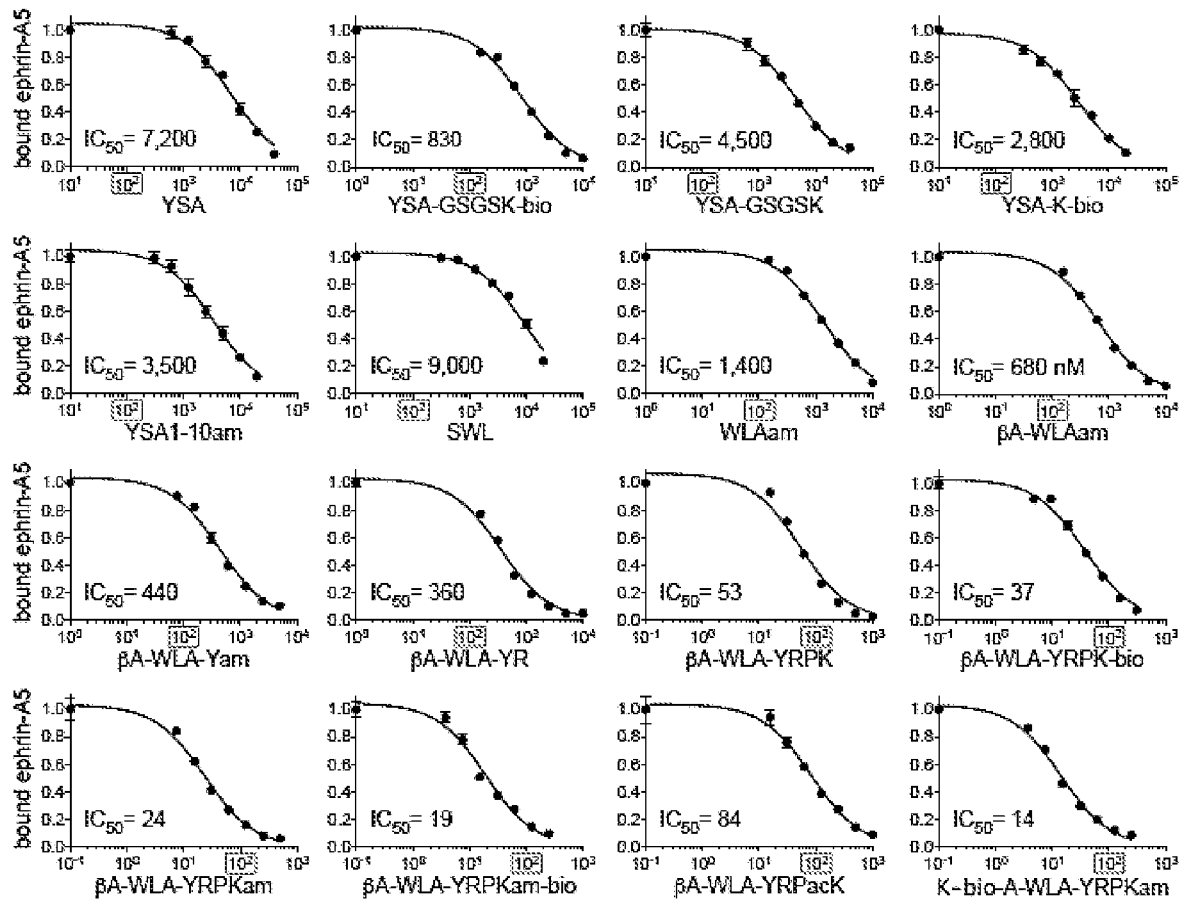
FIG. 2 shows potency and selectivity of EphA2-targeting peptides.
Figure 2:
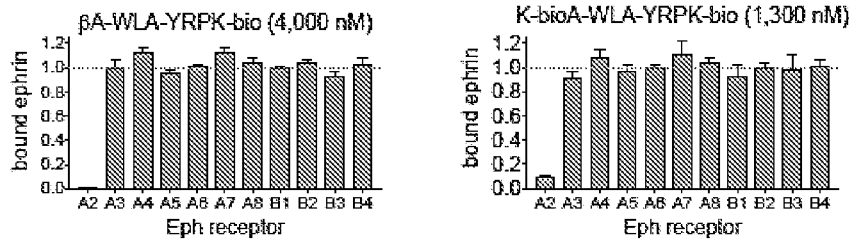
Figure 3:
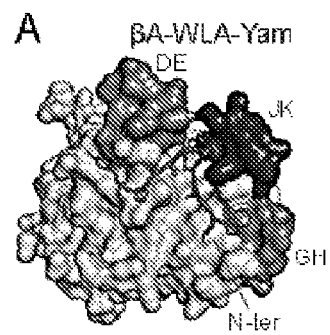
FIG. 3 shows the structures of three YSA derivative peptides bound to the EphA2 LBD.
Figure 3:
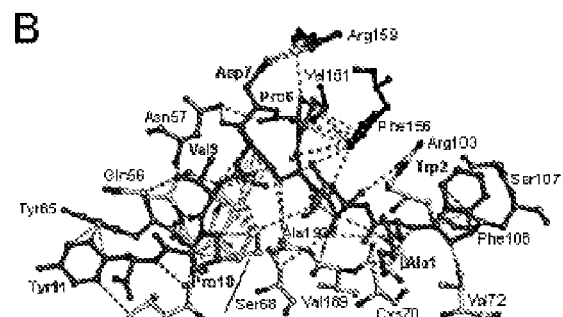
Figure 3:
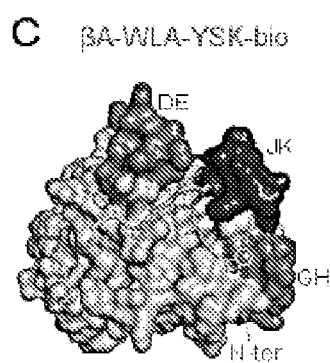
Figure 3:
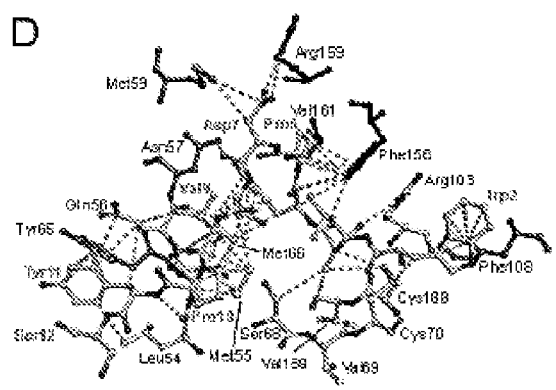
Figure 3:
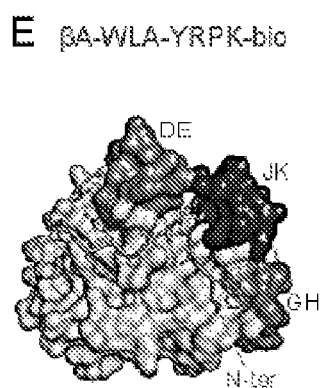
Figure 3:
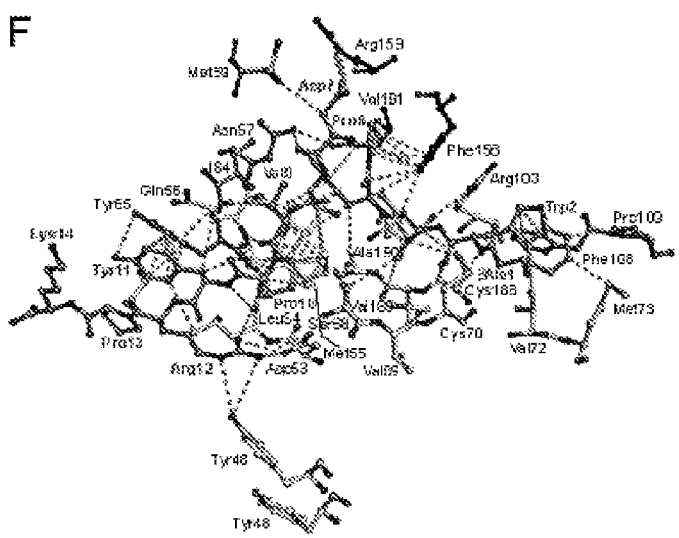

Although the crystal structure showed that only the first 10 amino acids of YSA stably interacted with the EphA2 LBD, additional electron density in the interface between the two EphA2 molecules of the asymmetric unit was observed, which was interpreted as the head-group of the biotin from one of the two peptide molecules (FIGS. 1A and 7A). The biotin interacted mainly with residues Thr45 and Tyr48 of the other EphA2 molecule in the asymmetric unit (FIGS. 7B, 7C). Consistent with a contribution of the biotin to EphA2 binding, ELISAs measuring inhibition of ephrin-A5-EphA2 interaction revealed that the YSA-GSGSK-bio peptide (SEQ ID NO: 12) was ~5 fold more potent than YSA-GSGSK (SEQ ID NO: 13), which contained the linker but not the biotin (Table 1 and FIG. 2A). In addition, the YSA1-10 am peptide (SEQ ID NO: 15) lacking the last two residues of YSA, which were not clearly visible in the crystal structure, was as potent as YSA (FIG. 2A and Table 1). This suggests that Met11 and Ser12 were not important for the interaction with EphA2, consistent with data from a previous alanine scan.

The other peptide previously identified by phage display, SWL, had some residues in common with YSA (FIG. 1G), suggesting that it may have been possible to incorporate SWL residues in YSA. It was found that replacement of Tyr1 and Ser2 of YSA with SWL residues Trp2 and Leu3, respectively, improved peptide potency by ~ 2 fold (Table 1 and FIG. 2A, compare WLAam with YSA1-10 am). Since an alanine scan showed a favorable effect of replacing Ser1 in SWL with Ala, the WLAam peptide was modified by adding an N-terminal βAla. This unnatural amino acid was an improvement to Ala, its addition to the peptide resulted in improved peptide resistance to proteolytic degradation by plasma aminopeptidases. This replacement further increased potency by ~ 2 fold (Table 1 and FIG. 2A, compare βA-WLAam (SEQ ID NO: 18) with WLAam). Replacement of Met10 with Tyr (the corresponding residue in SWL), improved potency by another ~2 fold (Table 1 and FIG. 2A, compare βA-WLA-Yam (SEQ ID NO: 19) with βA-WLAam (SEQ ID NO: 18)).

The crystal structure of the βA-WLA-Yam peptide (SEQ ID NO: 19) in complex with the EphA2 LBD, which was solved at a resolution of 1.53 Å, confirmed additional interactions with EphA2 that accounted for the increased potency (FIGS. 3A, 3B, 7D and 8B). For example, extended hydrophobic interactions of the βA-WLA-Yam peptide (SEQ ID NO: 19) were mediated by Trp2 and Tyr11. Further, βAla1 did not significantly interact with EphA2, this suggested that the observed ~2-fold increase in potency due to the addition of βAla1 was caused by the elimination of the N-terminal positive charge of the Trp residue.

Addition of Arg12, the residue present at the corresponding position of SWL, improved peptide solubility in aqueous solutions (Table 1 and FIG. 2A, compare βA-WLA-YR (SEQ ID NO: 25) with βA-WLA-Yam (SEQ ID NO: 19)). Since Arg12 could introduce sensitivity to proteolytic degradation of C-terminal peptide extensions, a proline was included at position 13 because arginine followed by a proline is resistant to cleavage by trypsin-like proteases. A lysine was also included at position 13 to allow attachment of biotin or other tags (Table 1, βA-WLA-YRPK (SEQ ID NO: 26)). Remarkably, the addition of both Pro13 and Lys14 increased potency by ~7 fold (Table 1 and FIG. 2A, compare βA-WLA-YRPK (SEQ ID NO: 26) with βA-WLA-YR (SEQ ID NO: 25)). The binding affinity of βA-WLA-YRPK (SEQ ID NO: 26) for the EphA2 LBD measured by isothermal titration calorimetry (ITC) was ~200 nM, which was a 50-fold improvement compared to YSA-GSGSK-bio (SEQ ID NO: 12) (Tables 1 and 3). The corresponding biotinylated peptide also exhibited much higher potency in ELISAs and much higher binding affinity measured by ITC (Tables 1 and 3; FIG. 2A, βA-WLA-YRPK-bio (SEQ ID NO: 27)). Replacement of Arg12 with Ser, to eliminate possible residual cleavage by trypsin-like proteases, yielded a peptide with only slightly decreased potency but with the disadvantage of not being soluble in aqueous solutions (Table 1, βA-WLA-YSPK-bio (SEQ ID NO: 28)).

The crystal structures of the βA-WLA-YRPK-bio peptide (SEQ ID NO: 27) in complex with the EphA2 LBD, solved in two different space groups at resolutions of 1.55 Å and 2.20 Å (FIGS. 3E, 3F, 7F, 8D, 9A and Table 2), explained the increased potency of this peptide. In one of the four complexes observed in the two structures, Arg12 interacted with EphA2 residues Asp53 and Tyr48. Peptide Pro13 packed against peptide Tyr11 and helped fill the hydrophobic pocket lined by EphA2 Leu54. In addition, the structures suggest that C-terminal amidation of βA-WLA-YRPK (SEQ ID NO: 26) could further improve potency by eliminating the C-terminal negative charge positioned near the negatively charged Glu40 of EphA2 (inset in FIG. 11D). The amidated βA-WLA-YRPKam (SEQ ID NO: 29) and βA-WLA-YRPKam-bio (SEQ ID NO: 30) peptides showed a ~2-fold higher potency than the peptides with an unmodified C-terminus (Table 1 and FIG. 2A).

Importantly, YSA derivatives with greatly increased potency described herein, such as βA-WLA-YRPK-bio (SEQ ID NO: 27), retained high specificity for EphA2 because even at concentrations 100-fold higher than the $IC_{50}$ value for inhibition of ephrin-A5-EphA2 binding, they did not inhibit ephrin binding to any other Eph receptor (FIG. 2B).

Example 3: C-Terminal Biotin and Negative Charge Potentiated the Agonistic Properties of YSA Derivatives The YSA-GSGSK-bio peptide (SEQ ID NO: 12) has been previously shown to be an agonist that induces EphA2 tyrosine phosphorylation and downstream signaling. The conserved tyrosine 588 (Y588) autophosphorylation site in the EphA2 juxtamembrane segment can be used as a marker indicative of EphA2 activation. Dose-response curves measuring Y588 phosphorylation of endogenous EphA2 expressed in PC3 prostate cancer cells stimulated with YSA-GSGSK-bio (SEQ ID NO: 12) yield an $EC_{50}$ value in the low micromolar range (FIG. 4A). Surprisingly, the non-biotinylated version of the peptide induced only a very small increase in Y588 phosphorylation, which is only detectable at high peptide concentration (FIG. 4B).

Figure 10:
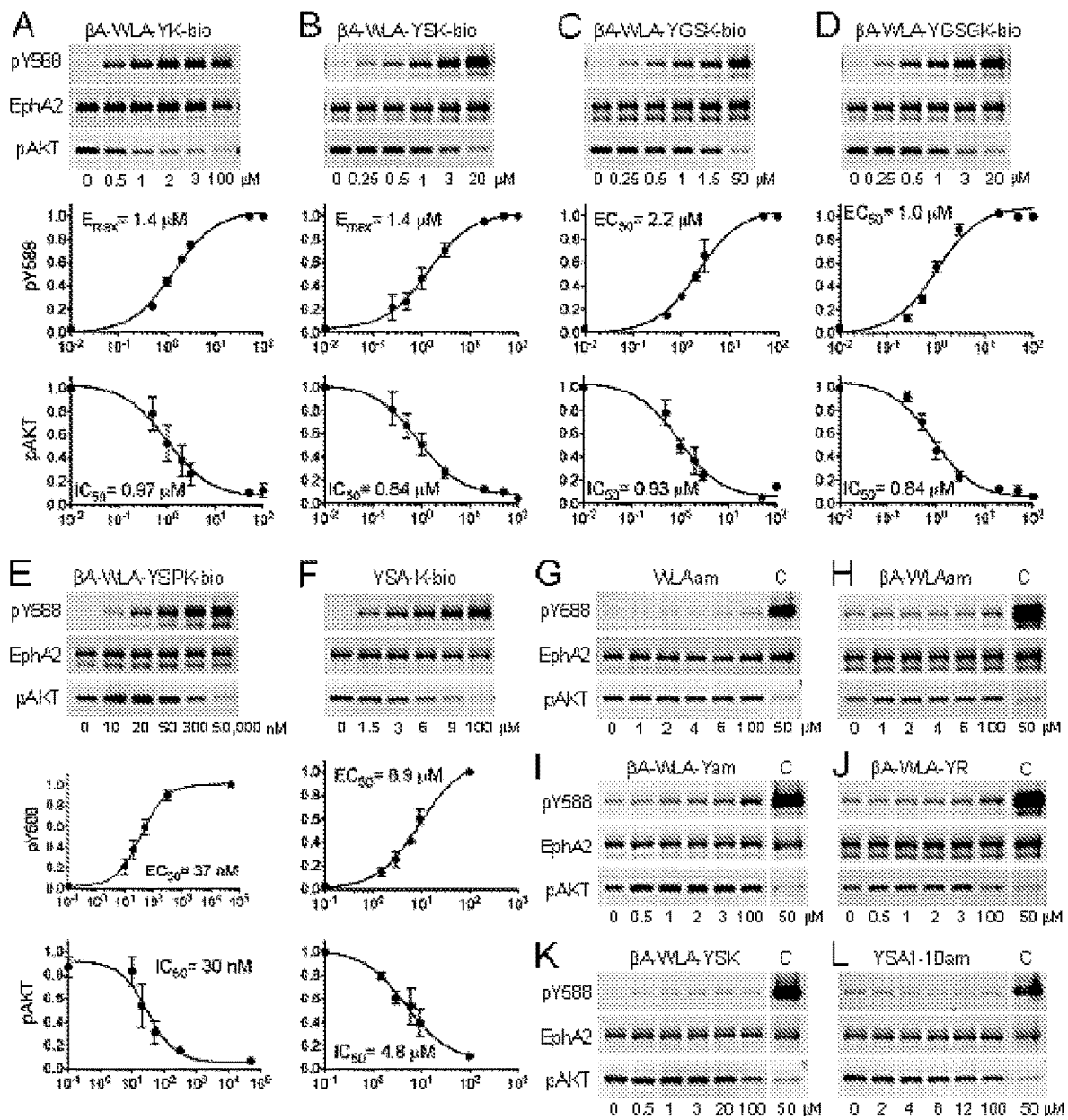
FIG. 10 shows that biotinylation dramatically promotes the agonistic properties of YSA derivative peptides. PC3 cells were treated for 15 min with different concentrations of the indicated peptides. The immunoblots show EphA2 autophosphorylation on tyrosine 588 (pY588, indicative of receptor activation), total EphA2 levels, and AKT phosphorylation on S473 (indicative of AKT activation).

The two most potent biotinylated peptides, βA-WLA-YRPK-bio (SEQ ID NO: 27) and βA-WLA-YRPKam-bio (SEQ ID NO: 30), were also agonists that induce high levels of EphA2 phosphorylation comparable to YSA-GSGSK-bio (SEQ ID NO: 12) (FIGS. 4C, 4D). However, as expected given their much higher potency, these two peptides were active at nanomolar concentrations (FIGS. 4B, 4C). These data suggest that the C-terminal biotin promoted the agonistic activity of YSA derivative peptides. The general role of the biotin in promoting EphA2 activation was confirmed by analysis of other biotinylated and non-biotinylated peptides (FIG. 10). These include another biotinylated/non-biotinylated pair (Table 1 and FIGS. 10A, 10K, βA-WLA-YSK-bio (SEQ ID NO: 21) and βA-WLA-YSK (SEQ ID NO: 22)) and the biotinylated peptides with C-terminal linkers of different lengths (Table 1 and FIG. 10A-10D). It was observed that all biotinylated peptides strongly activated EphA2 and that the precise position of the biotin (relative to the peptide residues interacting with the ephrin-binding pocket) did not have a strong effect on EphA2 activation. This was in agreement with the crystal structures, in which the linker regions, including the stem of the biotin, were poorly defined (FIG. 7A, 7D-7F), this suggested that these regions did not interact with EphA2. Thus, peptides with 1 to 7 residues between Pro10, which was conserved in all YSA derivatives, and the Lys-biotin residue can all efficiently activate EphA2. In contrast, the non-biotinylated peptides either did not detectably activate EphA2 or were very weak activators that induced barely detectable EphA2 Y588 phosphorylation only when they were present at high concentrations (Table 1 and FIG. 10G-10L).

The observation that C-terminal amidation of βA-WLA-YRPK-bio (SEQ ID NO: 27) increases its binding affinity and potency in ELISAs (Table 1) but decreases its agonistic potency in cells (FIGS. 4C, 4D), suggested that the negative charge of the unmodified peptide C-terminus may play a role in EphA2 activation. Indeed, it was found that the non-amidated βA-WLA-YRPK (SEQ ID NO: 26) had substantial ability to activate EphA2 in cells, even though the concentrations needed were about 10-fold higher than for the biotinylated peptide and the maximal Y588 phosphorylation induced by saturating peptide concentrations was about 40% lower (FIGS. 4C, 4E). Interestingly, the C-terminally amidated version of the peptide essentially lost the ability to activate EphA2 (FIG. 4F), consistent with a role of the C-terminal negative charge for EphA2 activation even in the absence of biotin.

To determine whether the loss of the positive charge in the side chain of Lys14 may contribute to the agonistic properties of the biotinylated peptides, a version of βA-WLA-YRPK (SEQ ID NO: 26) with acetylation of the Lys14 side chain was examined (Table 1, βA-WLA-YRPack (SEQ ID NO: 31)). It was found that the acetylated peptide had only slightly increased agonistic ability compared to βA-WLA-YRPK (SEQ ID NO: 26) (FIGS. 4E, 4G), this suggested that the Lys14 positive charge had only minor detrimental effects on EphA2 activation. This was consistent with a direct effect of the biotin in promoting EphA2 activation in cells.

Figure 4:
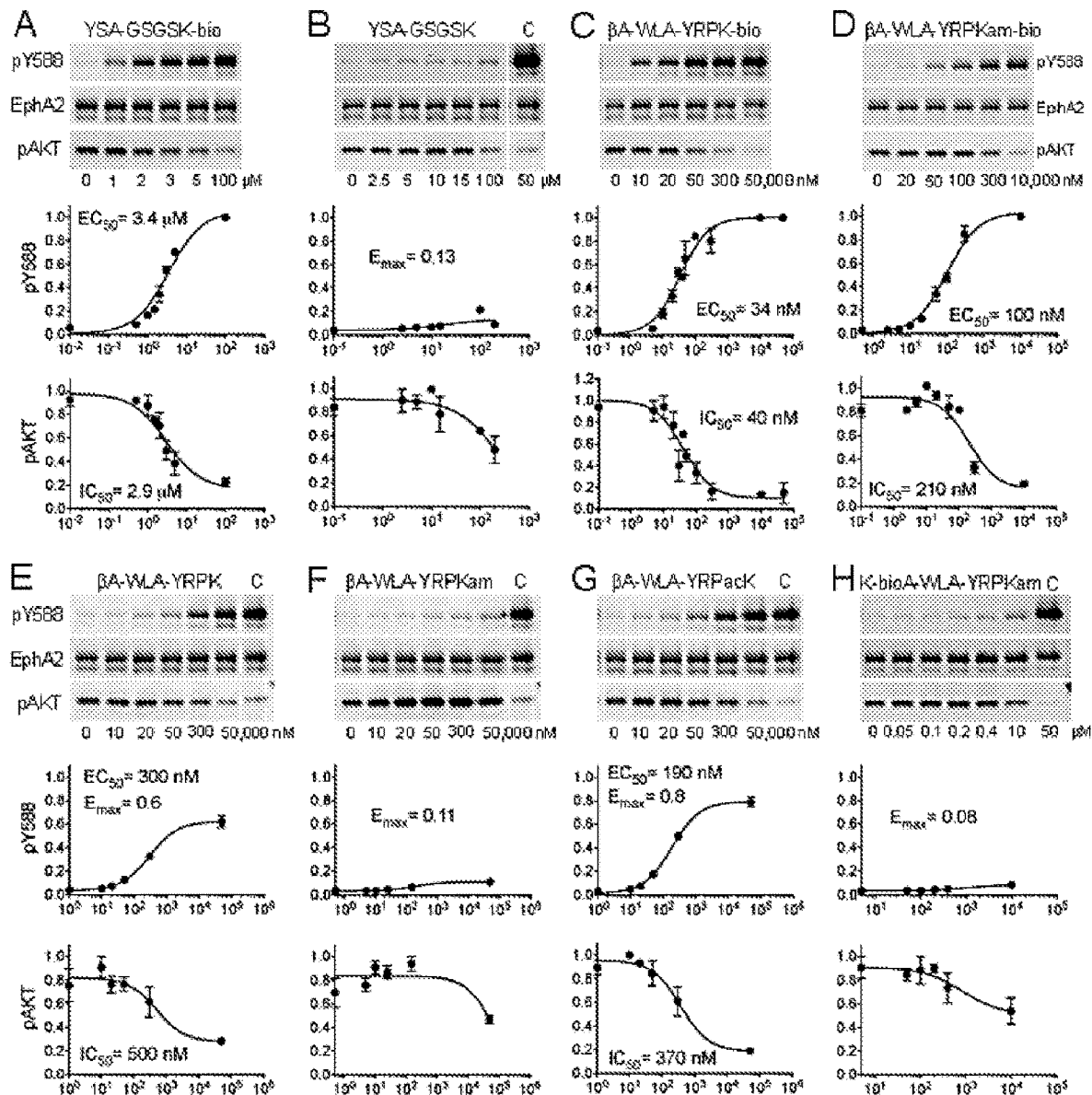
FIG. 4 shows the different YSA derivative peptides vary greatly in their ability to induce EphA2 signaling. PC3 cells were treated for 15 min with different concentrations of the indicated peptides. The immunoblots show EphA2 autophosphorylation on tyrosine 588 (pY588, indicative of receptor activation), total EphA2 levels, and AKT phosphorylation on S473 (indicative of AKT activation). The lane labeled C depicts cell lysate treated with YSA-GSGSK-bio (SEQ ID NO: 12) and run on the same gel for comparison. Maximal Y588 phosphorylation was similar for all biotinylated peptides, and thus the values were further normalized to the pY588 obtained with the highest peptide concentration. pY588 values for the non-biotinylated peptides were normalized to the value obtained with 50 μM YSA-GSGSK-bio (SEQ ID NO: 12) in the same blot. pAKT values were further normalized to the highest value observed without peptide or with low concentrations of peptide. Calculated $EC_{50}$ and $IC_{50}$ values and maximal (Emax) pY588 values for the non-biotinylated peptides relative to YSA-GSGSK-bio are also shown (SEQ ID NO: 12). The graphs show quantification of pY588 and pAKT from multiple blots (averages±SE), normalized to total EphA2 levels. The number of experiments analyzed is: 5 in FIG. 4A, 3 in FIG. 4B, 7 in FIG. 4C, 7 in FIG. 4D, 5 in FIG. 4E, 3 in FIG. 4F, 3 in FIG. 4G and 2 in FIG. 4H. Figure discloses SEQ ID NOS 12,-13, 27, 30, 26, 29, and 31-32, respectively, in order of appearance.
Figure 5:
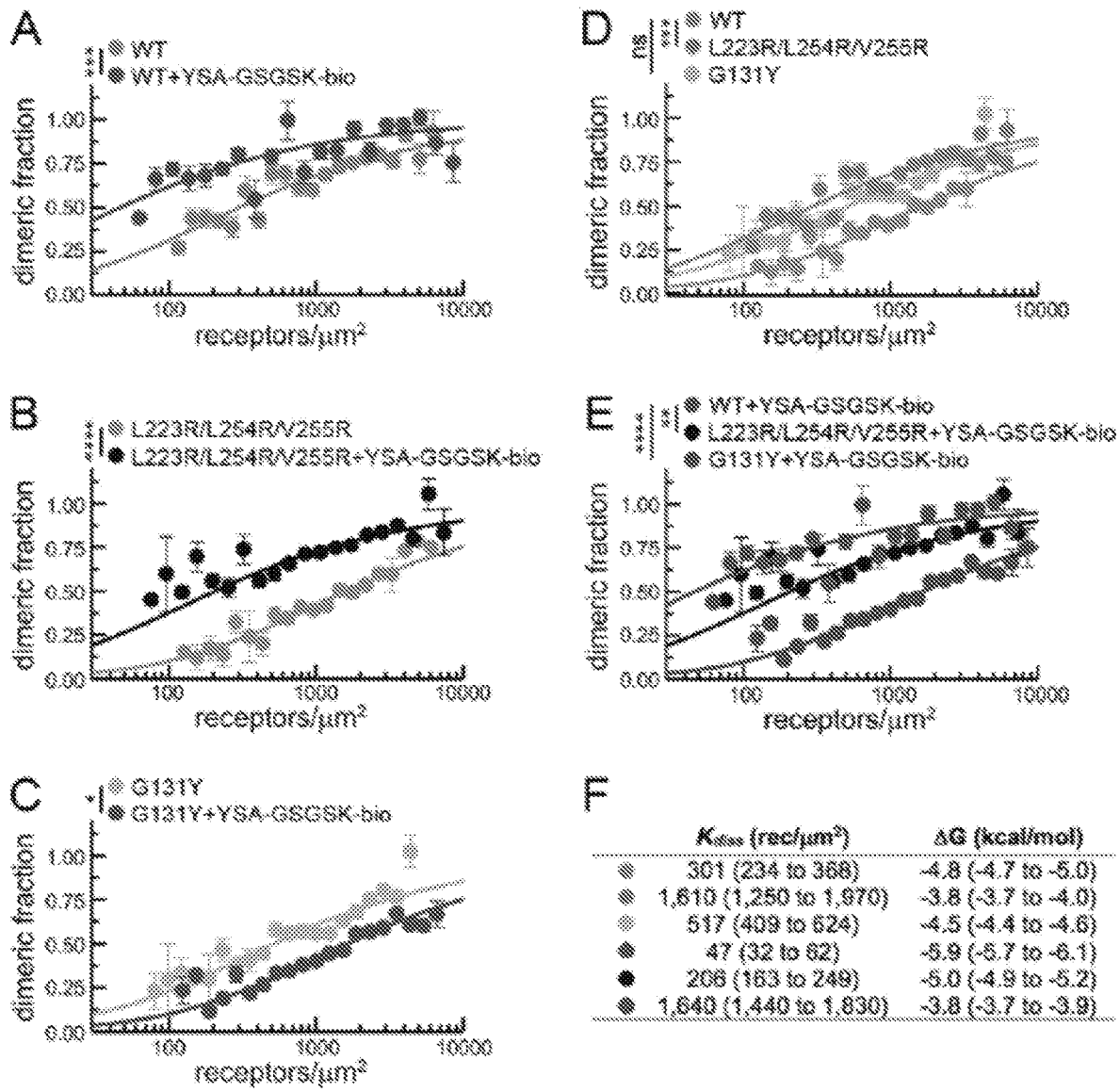
FIG. 5 shows YSA-GSGSK-bio (SEQ ID NO: 12) induces EphA2 oligomerization mainly through the dimerization interface. Dimerization curves obtained by fitting quantitative FRET data to a monomer-dimer model for comparison of EphA2 WT (FIG. 5A), L223R/L254R/V255 (FIG. 5B), and G131Y (FIG. 5C) with and without 50 μM YSA-GSGSK-bio peptide (SEQ ID NO: 12).
Figure 6:
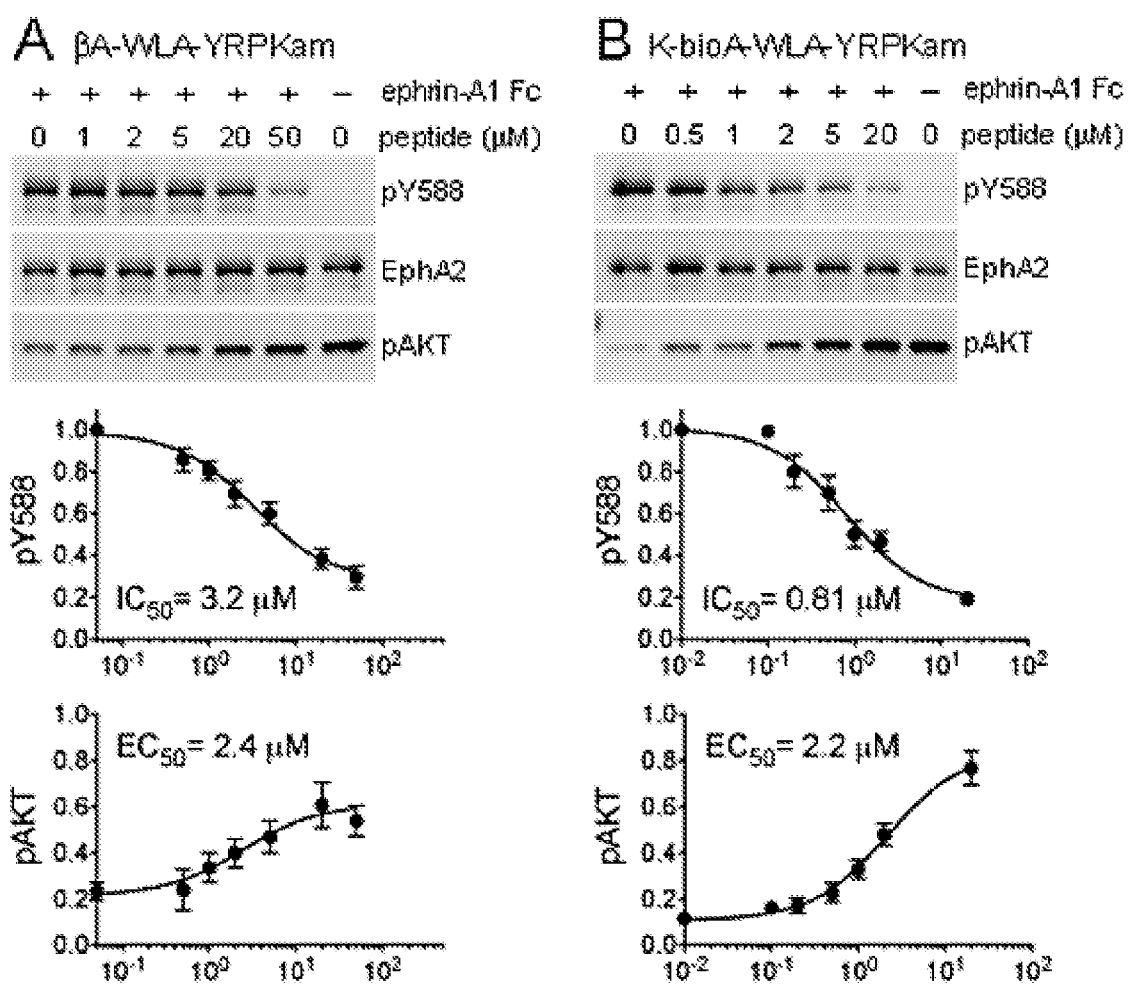
FIG. 6 shows YSA derivative peptides (βA-WLA-YRPKam (SEQ ID NO: 29) in FIG. 6A and Kbio-AWLA-YRPKam (SEQ ID NO: 32) in FIG. 6B) that do not activate EphA2 function as antagonists. PC3 cells were treated for 20 min with different concentrations of the indicated peptides and then activated with 0.1 μg/ml ephrin-A1 Fc. The immunoblots show EphA2 autophosphorylation on tyrosine 588 (pY588, indicative of receptor activation), total EphA2 levels, and AKT phosphorylation on S473 (indicative of AKT activation). pY588 values were normalized to the value obtained in the same blot with ephrin-A1 Fc treatment in the absence of peptide. pAKT values were normalized to the value obtained in the same blot without ephrin-A1 Fc or peptide treatment. Calculated $EC_{50}$ and $IC_{50}$ values are shown. The graphs show quantification of pY588 and pAKT from 7 blots for each peptide (averages±SE), normalized to total EphA2 levels.

The crystal structures of the peptides in complex with the EphA2 LBD provided insights into the mechanisms underlying the agonistic properties of the peptides. In the structures of two of the three biotinylated peptides, electron density for the biotin moiety of one of the two peptides in the asymmetric unit was observed (FIGS. 1A, 1E, 3C, 7A, 7E). In both structures, the biotin bound at the interface between two EphA2 LBD molecules and made similar contact with EphA2 residues (FIGS. 7B, 7C). This raised the possibility that, in cells, two biotinylated peptides bridge two EphA2 molecules, with each peptide binding to the ephrin-binding pocket of an EphA2 molecule and the "biotin-binding pocket" of another EphA2 molecule. In addition, the C-terminus of βA-WLA-YRPK (SEQ ID NO: 26) forms a salt bridge with Arg137 of the other EphA2 molecule in the asymmetric unit (FIG. 5D inset). The bivalent binding of biotinylated peptides could thus promote dimerization and reciprocal phosphorylation of EphA2 molecules, and in βA-WLA-YRPK-bio (SEQ ID NO: 27), this was further enhanced by the C-terminal negative charge. Interestingly, the four different structures with the three biotinylated peptides showed EphA2 dimers that interacted through the dimerization interface, whereas in the structure with the non-biotinylated βA-WLA-Yam peptide (SEQ ID NO: 19), the EphA2 molecules in the asymmetric unit interacted differently, through an interface that is incompatible with the orientation of the receptors on the cell surface (FIG. 11). According to the model described herein, an YSA derivative with biotin near the N-terminus should not efficiently activate EphA2 because such peptide would not simultaneously interact with the ephrin-binding pocket and the biotin-binding site. Indeed, it was found that the biotinylated K-bioA-WLA-YRPKam (SEQ ID NO: 32) did not efficiently activate EphA2 in cells, despite its low nanomolar potency in ELISAs (Table 1 and FIG. 4H). Interestingly, ITC measurements revealed that this peptide had by far the highest EphA2 binding affinity among the YSA derivatives that were engineered and are described herein (Tables 1 and 3).

The effects of YSA derivative peptides on AKT S473 phosphorylation were also noted, since EphA2 activation induced by ephrin-A ligands is known to inhibit AKT phosphorylation and activation. This confirmed that the peptide agonists promote not only EphA2 activation but also downstream signaling (FIGS. 4 and 10).

Example 4: The Peptide Agonists Promote EphA2 Oligomerization Through the "Dimerization" Interface Using a quantitative FRET approach in live cells, it was shown that, in transiently transfected HEK293 cells, YSA-GSGSK (SEQ ID NO: 13) promoted the formation of EphA2 dimers that assembled through an extracellular interface known as the "clustering" interface. Thus, the peptide enhanced the weak EphA2 dimerization observed in the absence of a bound ligand, which also occurred through the clustering interface. In contrast, the monomeric soluble form of ephrin-Al induced the formation of EphA2 dimers that assembled through another extracellular interface known as the "heterodimerization" or "dimerization" interface. To understand the effects of the YSA derivatives with agonistic properties on the assembly of EphA2 oligomers (dimers or higher order clusters), quantitative FRET experiments were performed with HEK293 cells expressing EphA2 tagged at the C-terminus with a donor (mTURQ) or acceptor (EYFP) fluorescent protein.

The FRET measurements revealed that the YSA-GSGSK-bio peptide (SEQ ID NO: 12) substantially increased the oligomeric fraction of EphA2 wild-type (WT) on the cell surface (FIG. 5A, 5F). YSA-GSGSK-bio (SEQ ID NO: 12) also promoted substantial oligomerization of the EphA2 L223R/L254R/V255R triple mutant, which had impaired ability to assemble through the clustering interface (FIG. 5B, 5F). In contrast, the biotinylated peptide had no effect on/reduced oligomerization of the EphA2 G131Y mutant, which had impaired ability to assemble through the dimerization interface (FIG. 5C, 5F). Comparison of the oligomerization curves of EphA2 WT and the two mutants in the absence of YSA-GSGSK-bio (SEQ ID NO: 12) shows that the L223R/L254R/V255R mutations impairs dimerization (FIG. 5D, 5F), while in the presence of the peptide the G131Y mutation strongly impaired dimerization and the triple mutation had a much smaller effect, suggesting that the biotinylated peptide mainly inducesd EphA2 dimerization through the dimerization interface (FIG. 5E, 5F). This approach was validated with the crystal structures, where the two EphA2 LBDs in the asymmetric unit interacted through the dimerization interface when bound to one of the three biotinylated peptides (FIG. 11A, 11C-11F) but not when bound to the non-biotinylated βA-WLA-Yam (SEQ ID NO: 19) (FIG. 11B). Thus, the FRET and X-ray crystallography data described herein show that the peptide agonists induced EphA2 activation and downstream signaling by promoting interaction of receptor molecules on the cell surface through the dimerization interface.

Example 5: YSA Derivatives Lacking Agonistic Properties Inhibit Ephrin-Induced EphA2 Activation and Signaling A number of the YSA derivatives appeared to be essentially inactive in the assays measuring EphA2 activation in cells (FIGS. 4 and 10). However, these peptides inhibited ephrin binding to EphA2 in ELISAs, some with low nanomolar potency (Table 1). To determine whether they could also inhibit EphA2 activation by ephrin-A ligands in cells, the effects of the two most potent peptides described herein were examined: βA-WLA-YRPKam (SEQ ID NO: 29) and Kbio-AWLA-YRPKam (SEQ ID NO: 32). This revealed that both peptides inhibited EphA2 Y588 phosphorylation induced by ephrin-Al Fc and thus could serve as antagonists (FIG. 6). They also prevented the inhibitory effects of EphA2 activation on AKT. Kbio-AWLA-YRPKam (SEQ ID NO: 32) was more effective, consistent with its low nanomolar EphA2 binding affinity (Tables 1 and 3).

While preferred embodiments of the present methods and compositions described herein have been shown, it will be obvious to those skilled in the art that such embodiments are provided by way of example only. Numerous variations, changes, and substitutions will now occur to those skilled in the art without departing from the methods and compositions described herein. It should be understood that various alternatives to the embodiments of the methods and compositions described herein may be employed in practicing the methods and compositions described herein. It is intended that the following claims define the scope of the methods and compositions described herein and that methods and structures within the scope of these claims and their equivalents be covered thereby.

TABLE 1

EphA2 Targeting Peptides
EphA2 Targeting Peptides

| Name | Sequence[1] | $IC_{50}$ (nM) by ELISA | $K_D$ (nM) by ITC | EphA2 PY588 | Mass (Da) | Solubility in PBS/H2O (mg/ml) |
|---|---|---|---|---|---|---|
| YSA | YSAYPDSVPMMS (SEQ ID NO: 11) | 3,500 ± 200 (3)[2] | nd | +/− | 1,348 | 10/15 |
| YSA-GSGSK-bio[3] | YSAYPDSVPMMSGSGSK-bio (SEQ ID NO: 12) | 820 ± 60 (37) | 9,800 ± 0 (2) | +++ | 1,990 | 15/15 |
| YSA-GSGSK | YSAYPDSVPMMSGSGSK (SEQ ID NO: 13) | 4,500 ± 600 (3) | 8,000 ± 1,000 (3) | + | 1,764 | 10/5 |
| YSA-K-bio | YSAYPDSVPMMSK-bio (SEQ ID NO: 14) | 2,500 ±300 (3) | nd | +++ | 1,702 | 10/10 |
| YSA1-10am | YSAYPDSVPMam (SEQ ID NO: 15) | 3.400 ± 400 (5) | nd | − | 1,128 | 10/10 |
| SWL | SWLAYPGAVSYR (SEQ ID NO: 16) | 3,200 ± 300 (3) | nd | +/− | 1,370 | 5/10 |
| WLAam | WLAYPDSVPMam (SEQ ID NO: 17) | 1,500 ± 100 (8) | nd | +/− | 1,177 | 0/0 |
| βA-WLAam | βAWLAYPDSVPMam (SEQ ID NO: 18) | 840 ± 80 (11) | nd | +/− | 1,248 | 10/10 |
| βA-WLA-Yam | βAWLAYPDSVPYam (SEQ ID NO: 19) | 410 ± 50 (9) | nd | +/− | 1,280 | 0/5 |
| βA-WLA-YK-bio | βAWLAYPDSVPYK-bio (SEQ ID NO: 20) | 730 ± 90 (3) | nd | +++ | 1,636 | 0/0 |
| βA-WLA-YSK-bio | βAWLAYPDSVPYSK-bio (SEQ ID NO: 21) | 300 ± 50 (6) | nd | +++ | 1,723 | 2/0 |
| βA-WLA-YSK | βAWLAYPDSVPYSK (SEQ ID NO: 22) | 380 ± 140 (3) | nd | − | 1,497 | 5/2 |
| βA-WLA-YGSK-bio | βAWLAYPDSVPYGSK-bio (SEQ ID NO: 23) | 400 ± 70 (3) | nd | +++ | 1,780 | 0/0 |
| βA-WLA-YGSGK-bio | βAWLAYPDSVPYGSGK-bio (SEQ ID NO: 24) | 330 ± 40 (3) | nd | +++ | 1,837 | 5/5 |
| βA-WLA-YR | βAWLAYPDSVPYR (SEQ ID NO: 25) | 390 ± 30 (3) | nd | + | 1,438 | 5/5 |
| βA-WLA-YRPK | βAWLAYPDSVPYRPK (SEQ ID NO: 26) | 55 ± 5 (6) | 190 ± 0 (2) | ++ | 1,663 | 10/10 |
| βA-WLA-YRPK-bio | βAWLAYPDSVPYRPK-bio (SEQ ID NO: 27) | 44 ± 5 (8) | 220 ± 10 (2) | +++ | 1,889 | 5/5 |

TABLE 1-continued EphA2 Targeting Peptides

| Name | Sequence[1] | IC$_{50}$ (nM) by ELISA | K$_D$ (nM) by ITC | EphA2 PY588 | Mass (Da) | Solubility in PBS/H2O (mg/ml) |
|---|---|---|---|---|---|---|
| βA-WLA-YSPK-bio | βAWLAYPDSVPYSPK-bio (SEQ ID NO: 28) | 62 ± 3 (3) | nd | +++ | 1,820 | 0/0 |
| βA-WLA-YRPKam | βAWLAYPDSVPYRPKam (SEQ ID NO: 29) | 19 ± 2 (6) | 110 ± 0 (2) | +/− | 1,662 | 10/10 |
| βA-WLA-YRPKam-bio | βAWLAYPDSVPYRPKam-bio (SEQ ID NO: 30) | 18 ± 1 (3) | nd | +++ | 1,888 | 2/5 |
| βA-WLA-YRP-ack | βAWLAYPDSVPYRPacK (SEQ ID NO: 31) | 82 ± 10 (3) | nd | ++ | 1,705 | 5/5 |
| K-bioA-WLA-YRPKam | K-bioAWLAYPDSVPYRPKam (SEQ ID NO: 32) | 13 ± 1 (3) | 27 ± 3 | +/− | 2,016 | 10/10 |
| CcamGA-WLA-YRPK-bio[4] | CcamGAWLAYPDSVPYRPK-bio (SEQ ID NO: 33) | 27 ± 7 (4) | nd | +++ | 2,106.2 | <0.1/5/10 |

[1]YSA residues are in black; residues used as spacers are in grey; SWL unique residues are in orange and other residues are in red.
[2]Averages ± SE are shown. The number of experiments is indicated in parentheses.
[3]Peptides crystallized in complex with the EphA2 LBD are in bold.
[4]Peptide CcamGA-WLA-YRPK-bio (SEQ ID NO: 33) has a purity of 97%; a calculated mass (Da) of 2,106.5; and an observed mass (Da) of 2,106.2;

TABLE 2

Crystallographic data collection and refinement of statistics

| | YSA-GSGSK-biotin | βA-WLA-Yam | βA-WLA-YRPK-biotin | | βA-WLA-YSK-biotin |
|---|---|---|---|---|---|
| Crystal | | | Crystal 1 | Crystal 2 | |
| PDB ID | 6NJZ | 6NK0 | 6NK1 | 6NK2 | 6NKP |
| Space group | I2 | P2$_1$ | P1 | P6$_1$ | P2$_1$2$_1$2$_1$ |
| Cell dimensions | | | | | |
| a, b, c (Å) | 44.78, 88.22, 153.41 | 46.80, 78.06, 58.34 | 44.69, 48.14, 50.21 | 154.44, 154.44, 51.91 | 60.92, 67.01, 93.11 |
| α, β, γ (°) | 90, 90.79, 90 | 90, 98.77, 90 | 99.39, 96.79, 90.20 | 90, 90, 120 | 90, 90, 90 |
| Comments | | tNCS with off origin peak at 0 0.5 0.5 with 39.5% intensity | | | |
| Crystallization conditions | 0.09M BIS TRIS pH 5.5, 22.5% w/v PEG 3,350, 3% w/v 6-aminohexanoic acid | 0.09M BIS TRIS pH 5.5, 22.5% w/v PEG 3,350, 3% w/v 6-aminohexanoic acid | 0.09M Sodium-Acetate pH 4.5, 22.5% w/v PEG 3,350, 3% w/v 6-aminohexanoic acid | 0.09M Sodium-Acetate pH 4.5, 22.5% w/v PEG 3,350, 3% w/v 6-aminohexanoic acid | 0.09M BIS-TRIS pH 5.5, 22.5% w/v PEG 3,350, 3% w/v 6-aminohexanoic acid |
| Data processing statistics | | | | | |
| Resolution (Å) | 28.98-1.90 (1.94-1.90) | 28.83-1.53 (1.55-1.53) | 27.60-1.55 (1.58-1.55) | 29.38-2.20 (2.27-2.20) | 29.39-2.03 (2.09-2.03) |
| R$_{merge}$ | 0.030 (0.501) | 0.035 (0.400) | 0.028 (0.091) | 0.149 (1.331) | 0.128 (0.674) |
| Reflections | 123795 (8181) | 220300 (7011) | 104127 (4822) | 397629 (26974) | 175409 (8939) |
| Unique Reflections | 44891 (2943) | 61846 (2631) | 52329 (2440) | 36732 (3157) | 24912 (1673) |
| I/σI | 10.9 (1.4) | 17.3 (2.0) | 12.3 (4.4) | 13.0 (1.6) | 13.2 (2.3) |
| CC$_{1/2}$ | 0.999 (0.672) | 0.999 (0.753) | 0.999 (0.976) | 0.998 (0.527) | 0.997 (0.714) |

TABLE 2-continued

Crystallographic data collection and refinement of statistics

| | YSA-GSGSK-biotin | βA-WLA-Yam | βA-WLA-YRPK-biotin | | βA-WLA-YSK-biotin |
|---|---|---|---|---|---|
| Completeness (%) | 95.7 | 98.2 | 87.9 | 100.0 | 98.9 |
|  | (93.0) | (85.0) | (83.4) | (100.0) | (92.3) |
| Redundancy | 2.8 | 3.6 | 2.0 | 10.8 | 7.0 |
|  | (28) | (2.7) | (2.0) | (8.5) | (5.3) |

Model

| | | | | | |
|---|---|---|---|---|---|
| EphA2/peptide complexes per asu | 2 | 2 | 2 | 2 | 2 |
| No. atoms (non-H) | | | | | |
|   EphA2/Peptide | 2925/171 | 3005/184 | 3013/245 | 2849/233 | 2848/204 |
|   Water | 209 | 395 | 411 | 160 | 271 |
|   Other solvent | 36 | 42 | 14 | 7 | 0 |

Refinement statistics

| | | | | | |
|---|---|---|---|---|---|
| Resolution (Å) | 24.58-1.90 | 28.83-1.53 | 27.61-1.55 | 29.38-2.20 | 28.95-2.03 |
|  | (1.94-1.90) | (1.55-1.53) | (1.58-1.55) | (2.26-2.20) | (2.11-2.03) |
| No. reflections | 44884 | 61808 | 52324 | 36706 | 24868 |
|  | (2581) | (2375) | (2619) | (2667) | (2567) |
| $R_{work}/R_{free}$ | 0.1693/0.2069 | 0.1512/0.1771 | 0.1457/0.1686 | 0.1882/0.2092 | 0.1675/0.2132 |
| R.m.s deviations | (0.2755/0.3667) | (0.2710/0.2535) | (0.1934/0.2138) | (0.2339/0.2575) | (0.2384/0.3156) |
|   Bond lengths (Å) | 0.006 | 0.013 | 0.008 | 0.003 | 0.012 |
|   Bond angles (°) | 1.024 | 1.319 | 1.031 | 0.712 | 1.171 |
| Ramachandran* | | | | | |
|   favored (%) | 95.4 | 97.29 | 96.51 | 96.26 | 95.92 |
|   allowed (%) | 4.6 | 2.7 | 3.5 | 3.5 | 4.1 |
|   outliers (%) | 0 | 0 | 0 | 0.27 | 0 |
| MolProbity Score/Percentile | 1.16/100th | 1.19/97th | 1.31/96th | 1.08/100th | 0.97/100th |

*Calculated with MolProbity

TABLE 3

Thermodynamic parameters of peptide-EphA2 interaction
(SEQ ID NOS 12-13, 26-27, and 29-32, respectively, in order of appearance)

Thermodynamic parameters of peptide-EphA2 interaction

| Name | $K_D$ (nM) | ΔG | ΔH (kcal/mol) | TΔS (kcal/mol) | N |
|---|---|---|---|---|---|
| YSA-GSGSK-bio | 9,800 ± 0 (2)[1] | −6.80 ± 0.01 | −25.99 ± 0.11 | 19.19 ± 0.12 | 0.83 ± 0.01 |
| YSA-GSGSK | 8,000 ± 1,000 (3) | −6.91 ± 0.07 | −22.40 ± 0.97 | 15.49 ± 0.97 | 0.79 ± 0.07 |
| βA-WLA-YRPK | 190 ± 0 (2) | −9.10 ± 0.01 | −32.38 ± 0.11 | 23.28 ± 0.12 | 0.89 ± 0.02 |
| βA-WLA-YRPK-bio | 220 ± 10 (2) | −9.01 ± 0.03 | −28.84 ± 0.46 | 19.83 ± 0.43 | 1.01 ± 0.01 |
| βA-WLA-YRPKam | 110 ± 0 (2) | −9.40 ± 0.01 | −30.65 ± 0.17 | 21.25 ± 0.16 | 0.96 ± 0.19 |
| K-bioA-WLA-YRPKam | 27 ± 3 (2) | −10.27 ± 0.04 | −24.56 ± 0.20 | 14.29 ± 0.16 | 1.06 ± 0.03 |

ΔG is the change in Gibbs energy,
ΔH is the change in enthalpy,
T is the absolute temperature,
ΔS is the change in entropy and
N is the binding stoichiometry.
[1]Averages ± SE are shown.
The number of experiments is indicated in parentheses.

TABLE 4

Purity and mass of EphA2-Targeting Peptides
(SEQ ID NOS 11-32, respectively, in order of appearance)
Purity and mass of EphA2-Targeting Peptides

| Name | Purity (%) | Calculated mass (Da) | Observed mass (Da) |
|---|---|---|---|
| YSA | 98.5 | 1,347.52 | 1,348.2 |
| YSA-GSGSK-bio1 | 95.9 | 1,990.25 | 1,990.2 |
| YSA-GSGSK | 98.0 | 1,763.95 | 1,763.7 |
| YSA-K-bio | 97.7 | 1,701.99 | 1,701.7 |
| YSA1-10am | 96.7 | 1,128.26 | 1,127.8 |
| SWL | 97.4 | 1,369.53 | 1,369.6 |
| WLAam | 96.9 | 1,177.38 | 1,177.4 |
| βA-WLAam | 97.5 | 1,248.49 | 1,248.5 |
| βA-WLA-Yam | 98.7 | 1,280.43 | 1,280.2 |
| βA-WLA-YK-bio | 97.2 | 1,635.92 | 1,636.0 |
| βA-WLA-YSK-bio | 90.3 | 1,722.96 | 1,722.9 |
| βA-WLA-YSK | 98.4 | 1,496.70 | 1,496.4 |
| βA-WLA-YGSK-bio | 98.9 | 1,780.05 | 1,780.2 |
| βA-WLA-YGSGK-bio | 95.2 | 1,837.10 | 1,837.3 |

TABLE 4-continued

Purity and mass of EphA2-Targeting Peptides
(SEQ ID NOS 11-32, respectively, in order of appearance)
Purity and mass of EphA2-Targeting Peptides

| Name | Purity (%) | Calculated mass (Da) | Observed mass (Da) |
|---|---|---|---|
| βA-WLA-YR | 96.0 | 1,437.60 | 1,437.6 |
| βA-WLA-YRPK | 98.7 | 1,662.92 | 1,663.2 |
| βA-WLA-YRPK-bio | 97.2 | 1,889.22 | 1,889.2 |
| βA-WLA-YSPK-bio | 98.7 | 1,820.11 | 1,819.8 |
| βA-WLA-YRPKam | 99.2 | 1,661.94 | 1,662.0 |
| βA-WLA-YRPKam-bio | 97.5 | 1,888.21 | 1,888.0 |
| βA-WLA-YRP-acK | 95.1 | 1,704.88 | 1,704.6 |
| K-bioA-WLA-YRPKam | 98.2 | 2,016.38 | 2,016.6 |

[1]Peptides crystalized in complex with the EphA2 LBD are in bold.

What is claimed is:

1. A composition comprising a peptide comprising β-A-X1-A-Y-P-D-S-V-P-X2 (SEQ ID NO: 1), wherein
   X1 is W-L; and
   X2 is any one of M-M-S, Mam, Yam, Y-K, Y-S-K, Y-G-S-K (SEQ ID NO: 2), Y-G-S-G-K (SEQ ID NO: 3), Y-R, or Y-S.

2. The composition of claim 1, wherein the peptide further comprises biotin on a carboxyl terminus ("C-terminal").

3. The composition of claim 1, wherein X2 is Y-R.

4. The composition of claim 3, wherein the peptide further comprises biotin on a carboxyl terminus ("C-terminal").

5. The composition of claim 1, wherein X2 is Mam, Yam, Y-K, Y-S-K, Y-G-S-K (SEQ ID NO: 2), Y-G-S-G-K (SEQ ID NO: 3), Y-R, or Y-S.

* * * * *